(12) United States Patent
Snider

(10) Patent No.: US 8,728,742 B2
(45) Date of Patent: May 20, 2014

(54) METHODS PREDICTING RISK OF AN ADVERSE CLINICAL OUTCOME

(75) Inventor: James V. Snider, San Diego, CA (US)

(73) Assignee: Critical Care Diagnostics, Inc., San Diego, CA (US)

( * ) Notice: Subject to any disclaimer, the term of this patent is extended or adjusted under 35 U.S.C. 154(b) by 0 days.

(21) Appl. No.: 13/422,574

(22) Filed: Mar. 16, 2012

(65) Prior Publication Data

US 2012/0276551 A1 Nov. 1, 2012

Related U.S. Application Data

(60) Provisional application No. 61/453,782, filed on Mar. 17, 2011.

(51) Int. Cl.
G01N 33/53 (2006.01)
G01N 33/68 (2006.01)
C07K 14/47 (2006.01)

(52) U.S. Cl.
USPC ............. 435/7.1; 530/350; 530/380; 530/396

(58) Field of Classification Search
None
See application file for complete search history.

(56) References Cited

U.S. PATENT DOCUMENTS

| | | | |
|---|---|---|---|
| 5,786,163 A | 7/1998 | Hall | |
| 6,040,147 A | 3/2000 | Ridker et al. | |
| 6,210,976 B1 | 4/2001 | Sabbadini et al. | |
| 6,288,218 B1 | 9/2001 | Levinson | |
| 6,323,334 B1 | 11/2001 | Kingsbury et al. | |
| 6,810,284 B1 | 10/2004 | Bradley | |
| 6,905,827 B2 | 6/2005 | Wohlgemuth et al. | |
| 7,087,396 B2 | 8/2006 | Tominaga et al. | |
| 7,432,060 B2 | 10/2008 | Lee | |
| 7,655,415 B2 | 2/2010 | Lee | |
| 7,670,769 B2 | 3/2010 | Lee | |
| 7,985,558 B2 | 7/2011 | Lee | |
| 7,989,210 B2 | 8/2011 | Lee | |
| 7,998,683 B2 * | 8/2011 | Snider et al. | 435/7.1 |
| 8,090,562 B2 * | 1/2012 | Snider et al. | 703/11 |
| 8,147,817 B2 | 4/2012 | Lee | |
| 8,420,785 B2 | 4/2013 | Snider | |
| 8,530,173 B2 | 9/2013 | Lee | |

(Continued)

FOREIGN PATENT DOCUMENTS

EP 1731910 12/2006
JP 2005-291899 10/2005

(Continued)

OTHER PUBLICATIONS

Christenson et al, 2010, Clinical Biochemistry. 43: 683-690.*

(Continued)

*Primary Examiner* — Zachary Howard
(74) *Attorney, Agent, or Firm* — Fish & Richardson P.C.

(57) ABSTRACT

Provided are methods for evaluating the risk of an adverse clinical outcome in a subject, deciding whether to discharge or continue treating a subject (e.g., on an inpatient basis), or to initiate or terminate treatment, selecting a subject for participation 5 in a clinical study, and selecting a therapeutic treatment for a subject that include determining a level of ST2 and a level of galectin-3 in a biological sample from the subject. Kits are also provided that contain an antibody that specifically binds to ST2, an antibody that specifically binds to galectin-3, and instructions for using the in the methods described.

33 Claims, 6 Drawing Sheets

(56) References Cited

U.S. PATENT DOCUMENTS

| | | | |
|---|---|---|---|
| 8,597,958 | B2 | 12/2013 | Lee |
| 8,617,825 | B2 | 12/2013 | Snider et al. |
| 2002/0115081 | A1 | 8/2002 | Lee et al. |
| 2002/0155513 | A1 | 10/2002 | Hsu et al. |
| 2003/0124624 | A1 | 7/2003 | Tominaga et al. |
| 2003/0228570 | A1 | 12/2003 | Yat Wah Tom et al. |
| 2004/0121343 | A1 | 6/2004 | Buechler et al. |
| 2004/0133079 | A1 | 7/2004 | Mazar et al. |
| 2005/0196817 | A1 | 9/2005 | Kingsmore et al. |
| 2005/0203046 | A1 | 9/2005 | Schmitz et al. |
| 2005/0250156 | A1 | 11/2005 | Shebuski et al. |
| 2005/0272054 | A1 | 12/2005 | Cargill et al. |
| 2006/0257946 | A1 | 11/2006 | Ding et al. |
| 2007/0042978 | A1 | 2/2007 | Girard et al. |
| 2007/0248981 | A1* | 10/2007 | Snider et al. ............. 435/6 |
| 2008/0193954 | A1 | 8/2008 | Pinto |
| 2009/0264779 | A1* | 10/2009 | Snider et al. ............ 600/508 |
| 2009/0305265 | A1 | 12/2009 | Snider et al. |
| 2010/0009356 | A1 | 1/2010 | Snider et al. |
| 2010/0055683 | A1 | 3/2010 | Snider et al. |
| 2011/0053170 | A1 | 3/2011 | Snider et al. |
| 2011/0262941 | A1 | 10/2011 | Snider et al. |
| 2012/0040381 | A1 | 2/2012 | Snider et al. |
| 2012/0065897 | A1 | 3/2012 | Snider et al. |
| 2012/0276551 | A1 | 11/2012 | Snider |
| 2013/0071404 | A1 | 3/2013 | Snider et al. |
| 2013/0177931 | A1 | 7/2013 | Snider |
| 2013/0244236 | A1 | 9/2013 | Snider et al. |
| 2013/0251664 | A1 | 9/2013 | Lee |
| 2013/0273562 | A1 | 10/2013 | Lee |
| 2013/0317030 | A1 | 11/2013 | Lee |

FOREIGN PATENT DOCUMENTS

| | | |
|---|---|---|
| WO | 00/35473 | 6/2000 |
| WO | 00/35951 | 6/2000 |
| WO | 00/73498 | 12/2000 |
| WO | 01/70817 | 9/2001 |
| WO | 02/38794 | 5/2002 |
| WO | 2004/056868 | 7/2004 |
| WO | 03/094856 | 3/2005 |
| WO | 2005/041893 | 5/2005 |
| WO | 2005/079844 | 9/2005 |
| WO | 2007/127749 | 11/2007 |
| WO | 2007/130627 | 11/2007 |
| WO | 2007/130962 | 11/2007 |
| WO | 2007/131031 | 11/2007 |
| WO | 2007/143295 | 12/2007 |
| WO | 2009/129454 | 10/2009 |
| WO | 2011/127412 | 11/2011 |

OTHER PUBLICATIONS

Shah et al., European Journal of Heart Failure, 12:826-832(2010).
Shimpo et al., Journal of the American Heart Association, 109:2186-2190(2004).
International Search Report issued in corresponding International Patent Application No. PCT/US2012/029500, mailed Nov. 30, 2012.
Written Opinion of the International Searching Authority issued in corresponding International Patent Application No. PCT/US2012/029500, mailed Nov. 30, 2012.
U.S. Appl. No. 13/787,975, filed Mar. 7, 2013, Snider et al.
U.S. Appl. No. 13/897,249, filed May 17, 2013, Snider et al.
U.S. Appl. No. 13/972,596, filed Aug. 21, 2013, Snider et al.
U.S. Appl. No. 13/969,116, filed Aug. 16, 2013, Snider.
Sharma et al., "Galectin-3 marks activated macrophages in failure-prone hypertrophied hearts and contributes to cardiac dysfunction," Circulation 110(19):3121-3128 (2004).
De Boer et al., "Galectin-3: A novel mediator of heart failure development and progression," Eur. J. Heart Fail. 11(9):811-817 (2009).
Yang et al., "Galectins: structure, function and therapeutic potential," Expert Rev. Mol. Med. 10:e17-e39 (2008).
Lok et al., "Prognostic value of galectin-3, a novel marker of fibrosis, in patients with chronic heart failure: data from the DEAL-HF study," Clin. Res. Cardiol. 99(5):323-328 (2010).
De Boer et al., "Predictive value of plasma galectin-3 levels in heart failure with reduced and preserved ejection fraction," Ann. Med. p. 1-9 (2010).
Supplemenary Material for De Boer et al., "Predictive value of plasma galectin-3 levels in heart failure with reduced and preserved ejection fraction," Ann. Med. p. 1-9 (2010).
Lok et al., "Galectin-3, a novel marker of macrophage activity, predicts outcome in patients with stable chronic heart failure," JACC, Abstracts—Cardiac Function and Heart Failure, p. 98A, Abstract 845-8 (Mar. 6, 2007).
International Preliminary Report on Patentability issued for PCT/US2012/029500 issued Sep. 17, 2013.
Communication Pursuant to Article 94(3) EPC for European Patent Application No. 11177461.8-1405 mailed Aug. 2, 2013.
Notice of Reasons for Rejection for Japanese Patent Application No. 2011-505224, mailed Sep. 4, 2013.
Extended European Search Report for European Patent Application No. 13179055.2-1408, mailed Sep. 9, 2013.
Van Kimmenade et al., "Utility of amino-terminal pro-brain natriuretic peptide, galectin-3, and apelin for the evaluation of patients with acute heart failure," J. Am. Coll. Cardiol. 48(6):1217-24 (2006).
Albert et al., "Prospective study of C-reactive protein, homocysteine, and plasma lipid levels as predictors of sudden cardiac death," Circulation 105(22):2595-2599 (2002).
Anwaruddin et al., "Renal function, congestive heart failure, and amino-terminal pro-brain natriuretic peptide measurement: results from the ProBNP investigation of dyspnea in the Emergency Department (PRIDE) Study," J. Am. Coll. Cardiol. 47(1):91-97 (2006).
Auer et al., "C-reactive protein and coronary artery disease," Jpn Heart J. 43(6):607-619 (2002).
Baekkevold et al., "Molecular characterization of NF-HEV, a nuclear factor preferentially expressed in human high endothelial venules," Am. J. Path. 163(1):69-79 (2003).
Baggish et al., "A validated clinical and biochemical score for the diagnosis of acute heart failure: The ProBNP Investigation of Dyspnea in the Emergency Department (PRIDE) Acute Heart Failure Score," Am. Heart J. 151:48-54 (2006).
Baumgarten et al., "Cytokines as emerging targets in the treatment of heart failure," Trends Cardiovasc Med. 10(5):216-223 (2000).
Bayes-Genis Antoni, "The circulating NTproBNP level, a new biomarker for the diagnosis of heart failure in patients with acute shortness of breath," Revista Espanola de Cardiolgiz 58(10):1142-1144 (2005).
Blum et al., "Pathophysiological role of cytokines in congestive heart failure," Annu. Rev. Med. 52:15-27 (2001) (Abstract).
Boisot et al., "Serial Sampling of ST2 Predicts 90-Day Mortality Following Destabilized Heart Failure," Journal of Cardiac Failure 14:732-738 (2008).
Brint et al., "ST2 is an inhibitor of interleukin 1 receptor and Toll-like receptor 4 signaling and maintains endotoxin tolerance," Nat. Immunol. 5(4):373-379 (2004).
Bruneau, "Selective changes in natriuretic peptide and early response gene expression in isolated rat atria following stimulation by stretch or endothelin-1," Cardiovasc. Res., 28(10):1519-1525 (1994).
Brunner et al., "Increased levels of soluble ST2 protein and IgG1 production in patients with sepsis and trauma," Intensive Care Med. 30(7):1468-1473 (2004).
Carter et al., "Regulation of ST2L expression of T helper (Th) type 2 cells," Eur. J. Immunol. 31(10):2979-2985 (2001) (Abstract only).
Chan et al., "Human IL-18 receptor and ST2L are stable and selective markers for the respective type 1 and type 2 circulating lymphocytes," J. Immunol. 167(3):73-75 (2005).
Conklin, B. "B-type Natriuretic peptide: a new measurement to distinguish cardiac from pulmonary causes of actue dyspnea," Journal fo Emergency Nursing 31(1):73-75 (2005).
Coyle et al., "Crucial role of the interleukin 1 receptor family member T1/ST2 in T helper cell type 2-mediated lung mucosal immune responses," J. Exp. Med. 190(7):895-902 (1999).

(56) References Cited

OTHER PUBLICATIONS

Dhalla et al., "Measurement of adrenolutin as an oxidation product of catecholamines in plasma," Mol. Cell. Biochem. 87:85-92 (1989).

ELECSYS® ProBNP assay, Roche Diagnostics, Indianapolis, IN, package insert v.7, Jul. 2007.

Feldman et al., "C-reactive protein is an independent predictor of mortality in women with HIV-1 infection," J. Acquir. Immune Defic. Syndr. 32(2):210-214 (2003) (Abstract).

Figal et al., "Usefulness of NTproBNP in the emergency management of patients with severe dyspnea and an uncertain heart failure diagnosis", Revista Espanola de Cardiologia 58(10):1155-1161 (2005).

Forssmann et al., "The heart is the center of a new endocrine, paracrine, and neuroendocrine system," Arch. Histol. Cytol. 52 Suppl:293-315 (1989)(Abstract).

Galvani et al., "Prognostic influence of elevated values of cardiac troponin I in patients with unstable angina," Circulation 95(8):2053-2059 (1997) (Abstract).

Gegenhuber et al., "B-type natriuretic peptide and amino terminal proBNP predict one-year mortality in short of breath patients independently of the baseline diagnosis of acute destabilized heart failure," Clinica Chimica Acta 370(1-2):174-179 (2006).

GenBank Acc. No. NM_003856.2, Jan. 24, 2003.
GenBank Acc. No. NM_016232.4, Jan. 24, 2003.
GenBank Acc. No. NM_033439.2, Aug 31, 2004.
GenBank Acc. No. NP_003847.2, Jan. 24, 2003.
GenBank Acc. No. NP_057316.3, Jan. 24, 2003.
GenBank Acc. No. NP_254274.1, Sep. 12, 2001.

Goetze et al., "B-type natriuretic peptide and its precursor in cardiac venous blood from failing hearts," European Journal of Heart Failure 7(1):69-74 (2005).

Gwechenberger et al., "Cardiac myocytes produce interleukin-6 in culture and in viable border zone of reperfused infarctions," Circulation 99(4):546-551 (1999).

Heeschen et al., "Predictive value of C-reactive protein and troponin T in patients with unstable angina: a comparative analysis. CAPTURE Investigators. Chimeric c7E3 antiPlatelet therapy in unstable angina refractory to standard treatment trial," J Am. Coll. Cardiol. 35(6):1535-1542 (2000) (Abstract only).

Information Hyperlinked Over Proteins—Symbol IL1RL1, 2006.

Iwahana et al., "Different promoter usage and multiple transcription initiation sites of the interleukin-1 receptor-related human ST2 gene in UT-7 and TM12 cells," Eur. J. Biochem. 264(2):397-406 (1999).

Januzzi et al., "Measurement of the Interleukin Family Member ST2 in Patients with Acute Dyspnea: Results from the PRIDE (Pro-Brain Natriuretic Peptide Investigation of Dyspnea in the Emergency Department) Study," J. Am. Coll. Cardiol. 50:607-613 (2007).

Januzzi et al., "Natriuretic peptide testing for the evaluation of critically ill patients with shock in the intensive care unit: a prospective cohort study," Crit. Care 10(1):R37 (2006).

Januzzi et al., "NT-proBNP testing for diagnosis and short-term prognosis in acute destabilized heart failure: an international pooled analysis of 1256 patients: the International Collaborative of NT-proBNP Study," Eur. Heart J. 27(3):330-337 (2006).

Januzzi et al., "The N-terminal Pro-BNP investigation of dyspnea in the emergency department (PRIDE) study," Am. J. Cardiol. 95(8):948-954 (2005).

Januzzi et al., "The value of soluble ST2 measurement for the diagnostic and prognostic evaluation of patients with acute dyspnea," Circulation 114(18):721 (2006) (Abstract).

Januzzi et al., "Utility of amino-terminal pro-brain natriuretic peptide testing for prediction of 1-year mortality in patients with dyspnea treated in the emergency department," Arch. Intern. Med. 166(3):315-320 (2006).

Kakkar et al., "The IL-33/ST2 pathway: Therapeutic target and novel biomarker," Nature Reviews Drug Discovery 7(10):827-840 (2008).

Kida et al., "Pathophysiological role of natriuretic peptides," Rinsho Byori 37(8):875-882 (1989) (Abstract only).

Kieser et al., "Identification of the primary growth response gene, ST2/T1, as a gene whose expression is differentially regulated by different protein kinase C isozymes," FEBS Lett. 372(2-3):189-193 (1995).

Knudsen et al., "Predictors of elevated B-type natriuretic peptide concentrations in dyspneic patients without heart failure: an analysis from the breathing not properly multinational study," Ann. Emerg. Med. 45(6):573-580 (2005).

Krauser et al., "Effect of body mass index on natriuretic peptide levels in patients with acute congestive heart failure: a ProBNP Investigation of Dyspnea in the Emergency Department (PRIDE) substudy," Am. Heart J. 149(4):744-750 (2005).

Kumar et al., "Expression of ST2, an interleukin-1 receptor homologue, is induced by proinflammatory stimuli," Biochem. Biophys. Res. Com. 235(3):474-478 (1997).

Kumar et al., "ST2/T1 protein functionally binds to two secreted proteins from Balb/c 3T3 and human umbilical vein endothelial cells but does not bind interleukin 1," J. Biol. Chem. 270(46):27905-27913 (1995).

Kuroiwa et al., "Construction of ELISA system to quantify human ST2 protein in sera of patients," Hybridoma 19(2):151-159 (2000).

Kuroiwa et al, "Identification of human ST2 protein in the sera of patients with autoimmune diseases," Biochemical and Biophysical Research Communications 284:1104-1108 (2001).

Lammerding et al., "Mechanotransduction in cardiac myocytes", Ann. NY Acad. Sci. 1015:53-70 (2004).

Lee et al., "Novel markers for heart failure iagnosis and prognosis", Curr. Opin. Cardiol. 20(3):201-210 (2005).

Leyva et al., European Heart J. 19:1814-1822 (1998).

Lohning et al., "T1/ST2 is preferentially expressed on murine Th2 cells, independent of interleukin 4, interleukin 5, and interleukin 10, and important for Th2 effector function," Proc. Natl. Acad. Sci. U.S.A. 95(12):6930-6935 (1998).

Macgowan et al., "Circulating interleukin-6 in severe heart failure", Am. J. Cardiol. 15;79(8):1128-31 (1997).

Mackenna et al., "Role of mechanical factors in modulating cardiac fibroblast function and extracellular matrix synthesis," Cardiovasc Res. 46(2):257-63 (2000).

Maisel et al., "Bedside B-Type Natriuretic Peptide in the Emergency Diagnosis of Heart Failure With Reduced or Preserved Ejection Fraction," J. Am. Coll. Cardiol. 41:2010-2017 (2003).

Maisel et al., "Primary results of the Rapid Emergency Department Heart Failure Outpatient Trial (REDHOT). A multicenter study of B-type natriuretic peptide levels, emergency department decision making, and outcomes in patients presenting with shortness of breath," J. Am. Coll. Cardiol. 44(6):1328-1333 (2004).

Maisel et al., "Rapid measurement of B-type natriuretic peptide in the emergency diagnosis of heart failure," N. Engl. J. Med. 347(3):161-167 (2002).

Mann et al., "Stress activated cytokines and the heart," Cytokine Growth Factor Rev. 7(4):341-54 (1996).

McCord et al., "Relationship between obesity and B-type natriuretic peptide levels," Arch. Intern. Med. 164(20):2247-2252 (2004).

McCullough et al., "B-type natriuretic peptide and renal function in the diagnosis of heart failure: an analysis from the Breathing Not Properly Multinational Study," Am. J. Kidney Dis. 41(3):571-579 (2003).

Millenium Pharmaceuticals, Inc. "Millenium Pharmaceuticals identifies a key mediator of allergic immunie response," Press Release Oct. 4, 1999 (2 pages).

Mitcham et al., "T1/ST2 signaling establishes it as a member of an expanding interleukin-1 receptor family," J. Biol. Chem. 271(10):5777-83 (1996).

Moe et al., "Neurohormonal activation in severe heart failure: relations to patient death and the effect of treatment with flosequinan," Am. Heart. J. 139:587-95 (2000).

Monoclonal Antibody: Anti-Human ST2; Medical & Bioligical Laboratories Co., Ltd., Aug. 23, 2000 (2 pages).

Mueller et al., "Increased Plasma Concentrations of Soluble ST2 are Predictive for 1-Year Mortality in Patients with Acute Destabilized Heart Failure," Clinical Chemistry 54:752-756 (2008).

(56) References Cited

OTHER PUBLICATIONS

Mueller et al., "Use of B-type natriuretic peptide in the evaluation and management of acute dyspnea," New England Journal of Medicine 350(7):647-654 (2004).
Mukoyama et al., "Augmented secretion of brain natriuretic peptide in acute myocardial infarction," Biochem. Biophys. Res. Commun. 180(1):431-6 (1991) (Abstract).
Murphy et al., "Signaling and transcription in T helper development," Annu Rev Immunol. 18:451-94 (2000).
Ng et al., "Diagnosis of heart failure using urinary natriuretic peptides," Clin Sci (Lond). 106(2):129-33 (2004).
Nozaki et al., "Soluble tumor necrosis factor receptors are elevated in relation to severity of congestive heart failure," Jpn. Circ. J. 61:657-64 (1997).
O'Neill et al., "The IL-1 receptor/toll-like receptor superfamily: crucial receptors for inflammation and host defense," Immunol Today 21(5):206-9 (2000).
Ohki et al., "Identification of mechanically induced genes in human monocytic cells by DNA microarrays," J. Hypertens 20(4):685-691 (2002).
Ohtsuka et al., "Effect of beta-blockers on circulating levels of inflammatory and anti-inflammatory cytokines in patients with dilated cardiomyopathy," J. Am. Coll. Cardiol. 37(2):412-7 (2001).
Onda et al., "Identification of genes differentially expressed in canine vasospastic cerebral arteries after subarachnoid hemorrhage," Journal of Cerebral Blood Flow & Metabolsim 19:1279-1288 (1999).
Orus et al., "Prognostic value of serum cytokines in patients with congestive heart failure," J. Heart Lung Transplant 19:419-25 (2000).
Oshikawa et al., "Acute eosinophilic pneumonia with increased soluble ST2 in serum and bronchoalveolar lavage fluid," Respir. Med. 95(6):532-533 (2001).
Oshikawa et al., "Elevated Soluble ST2 Protein Levels in Sera of Patients with Asthma with an Acute Exacerbation," Am. J. Respir. Crit. Care Med. 164:277-281 (2001).
Oshikawa et al., "Expression and function of the ST2 gene in a murine model of allergic airway inflammation," Clin. Exp. Allergy 32(10):1520-1526 (2002).
Oshikawa et al., "Expression of ST2 in helper T lymphocytes of malignant pleural effusions," Am. J. Respir. Crit. Care Med. 165(7):1005-1009 (2002).
Oshikawa et al., "ST2 protein induced by inflammatory stimuli can modulate acute lung inflammation," Biochem. Biophys. Res. Commun. 299(1):18-24 (2002).
Perrier et al., Am. J. Respir. Crit. Care Med. 156(2):492-496 (1997).
Potter et al., "Mutations in the murine fitness 1 gene result in defective hematopoiesis," Blood 90(5):1850-7 (1997).
Richards et al., "Plasma N-terminal pro-brain natriuretic peptide and adrenormedullin: new neurohormonal predictors of left ventricular function and prognosis after myocardial infarction," Circulation 97:1921-1929 (1998).
Ridker et al., "Inflammation, aspirin, and the risk of cardiovascular disease in apparently healthy men," New England J. Med. 336:973-979 (1997).
Rohde et al., "Circulating cell adhesion molecules are correlated with ultrasound-based assessment of carotid atherosclerosis," Arterial Sclerotic Vasc. Biol. 18:1765-1770 (1998).
Rohde et al., "Plasma concentrations of interleukin-6 and abdominal aortic diameter among subjects without aortic dilatation," Arterial Sclerotic Vasc. Biol. 19:1695-1699 (1999).
Roig et al., "Serum interleukin-6 in congestive heart failure secondary to idiopathic dilated cardiomyopathy," Am. J. Cardiol. 82(5):688-90, A8 (1998).
Sabatine et al., "Multimarker approach to risk stratification in non-ST elevation acute coronary syndromes: simultaneous assessment of troponin I, C-reactive protein, and B-type natriuretic peptide," Circulation 105(15):1760-1763 (2002).
Saccani et al., "Divergent effects of LPS on expression of IL-1 receptor family members in mononuclear phagocytes in vitro and in vivo," Cytokine 10(10):773-80 (1998).
Schmitz et al., "IL-33, an interleukin-1-like cytokine that signals via the IL-1 receptor-related protein ST2 and induces T helper type 2-associated cytokines," Immunity 23(5):479-490 (2005).
Selvais et al., J. Card. Fail. 6(3):201-7 (2000) (Abstract only).
Shimizu et al., "Functional SNPs in the distal promoter of the ST2 gene are associated with atopic dermatitis," Hum. Mol. Genet. 14(19):2919-2927 (2005).
Shimpo et al., "Serum levels of the interleukin-1 receptor family member ST2 predict mortality and clinical outcome in acute myocardial infarction" Circulation 109(18):2186-2190 (2004).
Silver et al., Cong. Heart Fail. 10(5 suppl. 3):1-30 (2004).
Sims JE, "IL-1 and IL-18 receptors, and their extended family," Current Opinion in Immunology 14:117-122 (2002).
Strunk et al., "Impact of the history of congestive heart failure on the utility of B-type natriuretic peptide in the emergency diagnosis of heart failure: results from the Breathing Not Properly Multinational Study," Am. J. Med. 119(1):69 el-11 (2006).
Sussamn et al., "Dance band on the Titanic: Biomechanical signaling in cardiac hypertrophy," Circ. Res. 91(10):888-98 (2002).
Svensson et al., "Prognostic value of biochemical markers, 12-lead ECG and patient characteristics amongst patients calling for an ambulance due to a suspected acute coronary syndrome," Journal of Internal Medicine 255(4):469-477 (2004).
Tajima et al., "The increase in serum soluble ST2 protein upon acute exacerbation of idiopathic pulmonary fibrosis," Chest 124(4):1206-1214 (2003).
Tang et al., "Gene expression profiling during the transition to failure in TNF-α over-expressing mice demonstrates the development of autoimmune myocarditis," Journal of Molecular and Cellular Cardiology 36:515-30 (2004).
Tominaga et al., "Nucleotide sequence of a complementary DNA for human ST2," Biochim. Biophys. Acta. 1171:215-218 (1992).
Tominaga et al., "ST2 gene: a gene that is induced by growth stimulation and encoding a product highly similar to the interleukin 1 receptors," Seikagaku 67(5):356-64 (1995) (Japanese with translation).
Tominaga, FEBS Lett., "A putative protein of a growth specific cDNA from BALB/c-3T3 cells is highly similar to the extracellular portion of mouse interleukin 1 receptor," 258:301-304 (1989).
Townsend et al., "T1/ST2-deficient mice demonstrate the importance of T1/ST2 in developing primary T helper cell type 2 responses," J. Exp. Med. 191(6):1069-76 (2000).
Tsuchiya et al., "Th1, Th2 and activated T-cell marker and clinical prognosis in peripheral T-cell lymphoma unspecified comparison AILD, ALCL, lymphoblastic lymphoma and ATLL," Blood 103:236-241 (2003).
Tsutamoto et al., "Interleukin-6 spillover in the peripheral circulation increases with the severity of heart failure, and the high plasma level of interleukin-6 is an important prognostic predictor in patients with congestive heart failure," J. Am. Coll. Cardiol. 31(2):391-8 (1998).
Tung et al., "Utility of B-type natriuretic peptide for the evaluation of intensive care unit shock," Crit. Care Med. 32(8):1643-1647 (2004).
Vidal et al., "Prognostic value of cytokines and neurohormones in severe heart failure," Rev. Esp. Cardiol. 55(5):481-6 (2002).
Wang et al., "Expression of interleukin-1β, interleukin-1 receptor, and interleukin-1 receptor antagonist mRNA in rat carotid artery after balloon angioplasty," Biochem. Biophyl. Res. Comm. 271:138-143 (2000).
Weinberg et al., "Expression and regulation of ST2, an interleukin-1 receptor family member, in cardiomyocytes and myocardial infarction," Circulation 106(23):2961-2966 (2002).
Weinberg et al., "Identification of serum soluble ST2 receptor as a novel heart failure biomarker," Circulation 107(5):721-726 (2003).
Yamaoka et al., "Anti-inflammatory cytokine profile in human heart failure: behavior of interleukin-10 in association with tumor necrosis factor-alpha," Jpn. Circ. J. 63(12):951-6 (1999).
Yanagisawa et al., "Murine ST2 gene is a member of the primary response gene family induced by growth factors," FEBS Lett. 302(1):51-53 (1992).
Yanagisawa et al., "Presence of a novel primary response gene ST2L, encoding a product highly similar to the interleukin 1 receptor type 1," FEBS Lett. 318(1):83-87 (1993).

(56) References Cited

OTHER PUBLICATIONS

Yanagisawa et al., "The expression of ST2 gene in helper T cells and the binding of ST2 protein to myeloma-derived RPMI8226 cells," J. Biochem. 121(1):95-103 (1997).
Zebrack et al., "Usefulness of high-sensitivity C-reactive protein in predicting long-term risk of death or acute myocardial infarction in patients with unstable or stable angina pectoris or acute myocardial infarction," Am. J. Cardiol. (2002).
International Search Report for PCT/US2007/067333, mailed Jan. 23, 2008.
International Preliminary Report on Patentability for PCT/US2007/067333, issued Oct. 28, 2008.
Written Opinion of the International Searching Authority for PCT/US2007/067333, mailed Jan. 23, 2008.
Orntoft et al., "Genome-wide study of gene copy numbers, transcripts, and protein levels in pairs of non-invasive and invasive human transitional cell carcinomas," Mol. Cell.Proteomics 1:37-45 (2002).
Linares et al., "C-reactive protein (CRP) levels in systemic lupus erythematosus (SLE)," 5:66-69 (1986) (Abstract).
Supplementary European Search Report for EP07761219, completed Apr. 9, 2009.
Partial European Search Report for EP 11177461, completed Sep. 12, 2011.
European Search Report for EP 10 17 1764; completed Sep. 24, 2010.
Kip et al., "The problem with composite end points in cardiovascular studies," J. Am. Coll. Cardiol. 51:701-707 (2008).
Ordonez-Llamos et al., "A formula for combining ST2 and NT-pro-BNP enhances prognostic accuracy in patients with heart failure," Clin. Chem. 54:A99, (2008).
Tung et al., "Amino-terminal pro-brain natriuretic peptide for the diagnosis of acute heart failure in patients with previous obstructive airway disease," Annals. Emerg. Med. 48:66-74, (2006).
Notice of Reasons for Rejection; JP Appl. No. 2009-507931; Oct. 26, 2011; 3 pp.
Notice of Reasons for Rejection; JP 2009-507931; Aug. 20, 2012; 2 pp.
Requisition by the Examiner to Avoid Abandonment; CA 2,650,201; Dec. 15, 2011; 3 pp.
Requisition by the Examiner to Avoid Abandonment; CA 2,640,201; Aug. 19, 2010; 4 pp.
Examiner's First Report on Patent; GB Appl. No. 2007244927; Nov. 22, 2010; 5pp.
Prosecution File History for U.S. Appl. No. 13/422,574.
Prosecution File History for U.S. Appl. No. 13/282,111.
Morrison et al.; American College of Cardiology 39:202-209 (2002).
Ridker et al., England J. Medicine 324:836-843 (2000).
Aukrust et la., "Cytokine network in Congestive Heart Failure Secondary to Ischemic or Idiopathic Dilated Cardiomyopathy", Am. J. Cardiol. 83:376-382 (1999).
Chan et al., "Human IL018 Receptor and ST2L are Stable and Selective Markers for the Respective Type I and Type 2 Circulating Lymphocytes," J. Immunol. 167(3) 1238-1244 (2001).
Frangogiannis et al., "Resident Cardiac Mast Cells Degranulate and Release Preformed TNF-alpha, Initiating the Cytokine Cascade in Experimental Canine Myocardial Ischemia/Reperfusion," Circulation, 98(7): 699-710 (1998).
Sutton et al., "Left Ventricular Remodeling after Myocardial Infarction: Pathophysiology and Therapy," Circulation 101(25):2981-8 (2000).
Tominaga et al., "The Existence of a Growth-Specific DNA Binding Factor for the Promoter Region of Mouse ST2 Gene," FEBS Lett. 354(3):311-4 (1994).
International Preliminary Report on Patentability for PCT/Us2009/040941; issued Oct. 19, 2010.
International Search Report for PCT/US2009/040941, completed Dec. 2, 2009, mailed Dec. 3, 2009.
Written Opinion of the International Searching Authority for PCT/US2009/040941, completed Dec. 2, 2009, mailed Dec. 3, 2009.
Supplementary European Search Report and Search Opinion for European Application No. EP 09731842, search and opinion mailed Apr. 1, 2011, search completed Feb. 28, 2011.
Prosecution File History for U.S. Appl. No. 13/151,012 downloaded from U.S. Patent and Trademark Office website on Jul. 1, 2013.
Prosecution File History for U.S. Appl. No. 13/299,612 downloaded from U.S. Patent and Trademark Office website on Jul. 1, 2013.
Prosecution File History for U.S. Appl. No. 11/789,169 downloaded from U.S. Patent and Trademark Office website on Jul. 1, 2013.
Prosecution File History for U.S. Appl. No. 12/425,956 downloaded from U.S. Patent and Trademark Office website on Jul. 1, 2013.
EP 07761219; Apr. 9, 2009 Supplemental European Search Report.
Examination Report issued Nov. 22, 2010 in corresponding Australian Patent Application No. 2007244927.
Examination Report issued Aug. 19, 2010 in corresponding Canadian Patent Application No. 2,650,201.
Office Action; U.S. Appl. No. 13/179,173; Sep. 23, 2011; 8 pp.
Office Action; U.S. Appl. No. 13/179,173; Jan 19, 2012; 21 pp.
Office Action; U.S. Appl. No. 13/179,173; Oct. 26, 2012; 10 pp.
Office Action; U.S. Appl. No. 13/179,173; Mar. 1, 2013; 8 pp.
Amendment in Reply to Office Action filed in U.S. Appl. No. 13/179,173 on Nov. 15, 2011.
Amendment in Reply to Office Action filed in U.S. Appl. No. 13/179,173 on Jul. 18, 2012.
Amendment in Reply to Office Action filed in U.S. Appl. No. 13/179,173 on Feb. 11, 2013.
Amendment in Reply to Office Action filed in U.S. Appl. No. 13/179,173 on Jul. 1, 2013.
Notice of Allowance issued in U.S. Appl. No. 13/179,173 on Aug. 26, 2013.
Communication issued in European Patent Application No. 11177461.8-1405 on Aug. 2, 2013.
Communication Pursuant to 94(3) EPC, European Patent Application No. 09731842.2, mailed Nov. 13, 2012, 3 pages.

\* cited by examiner

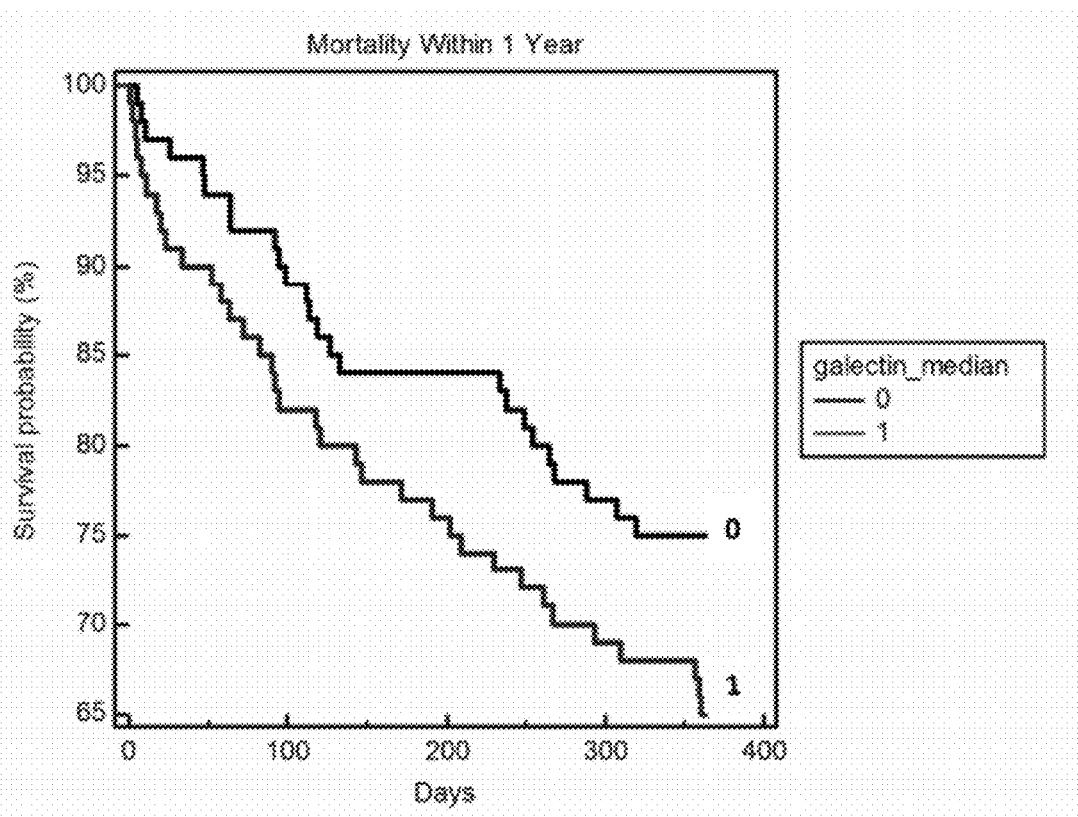

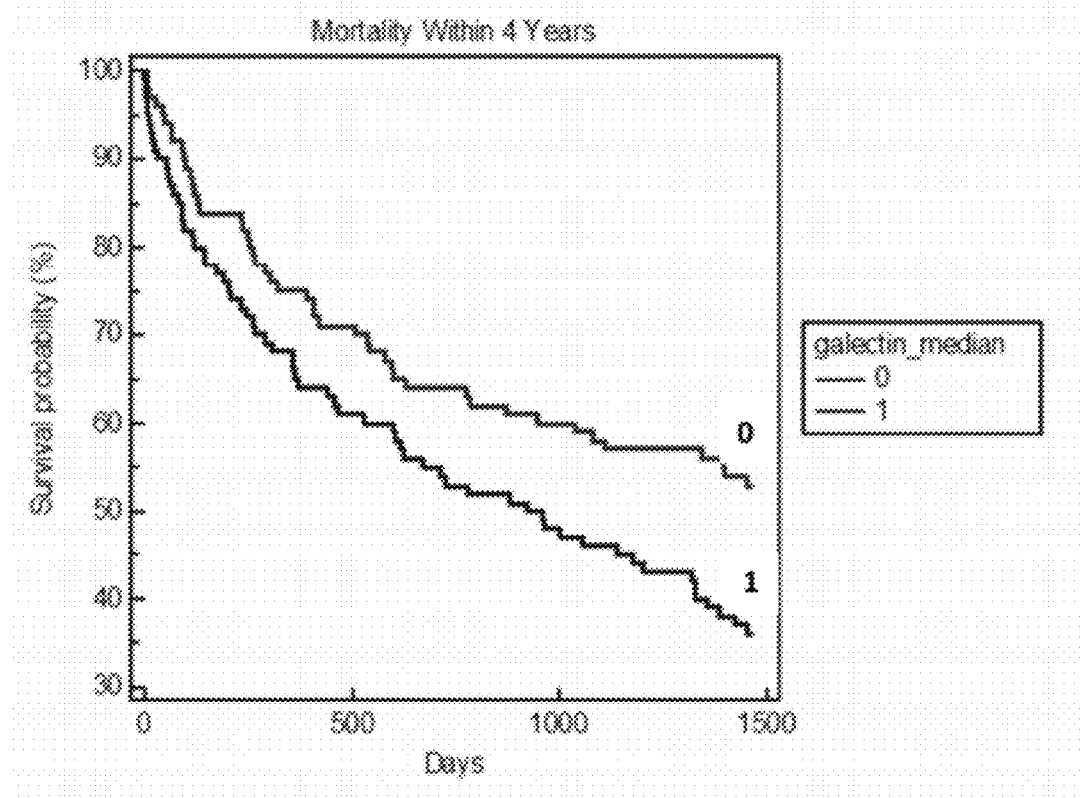

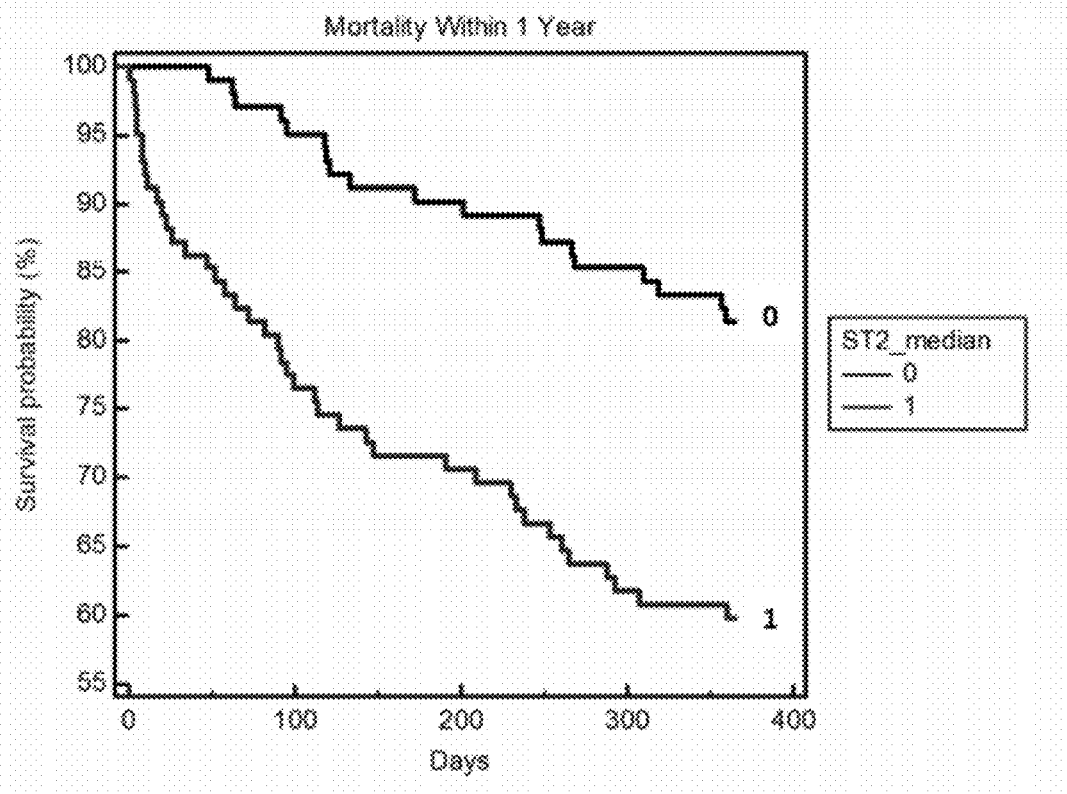

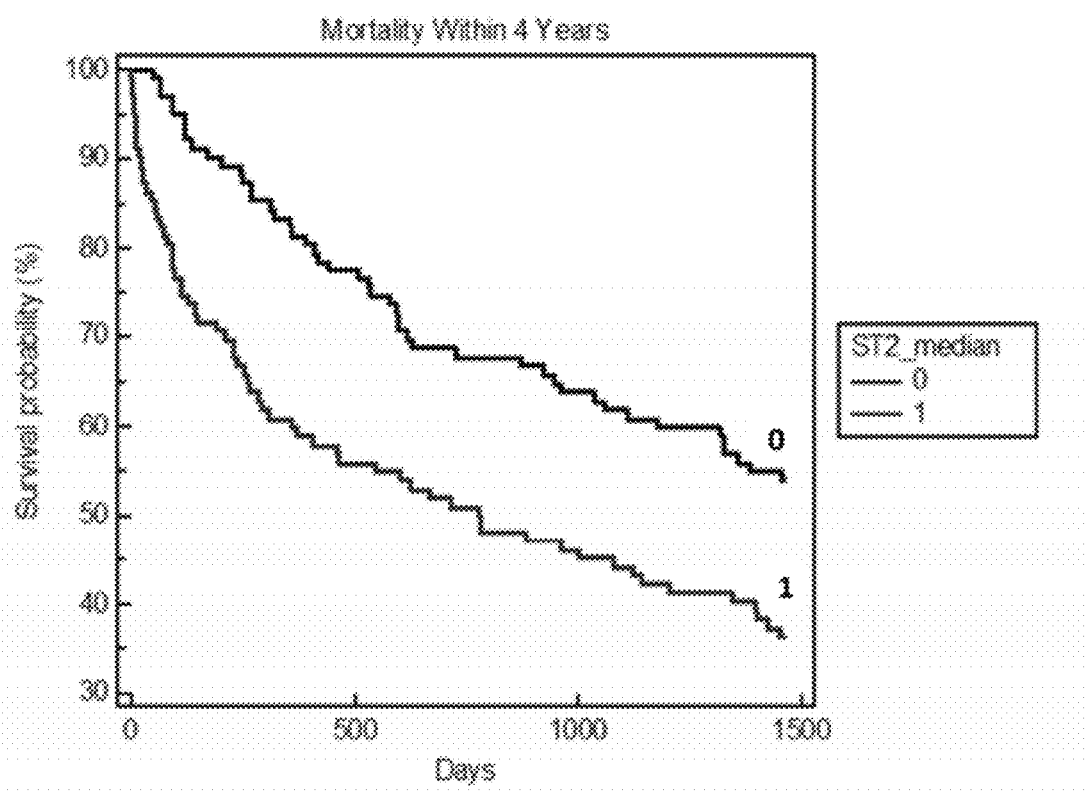

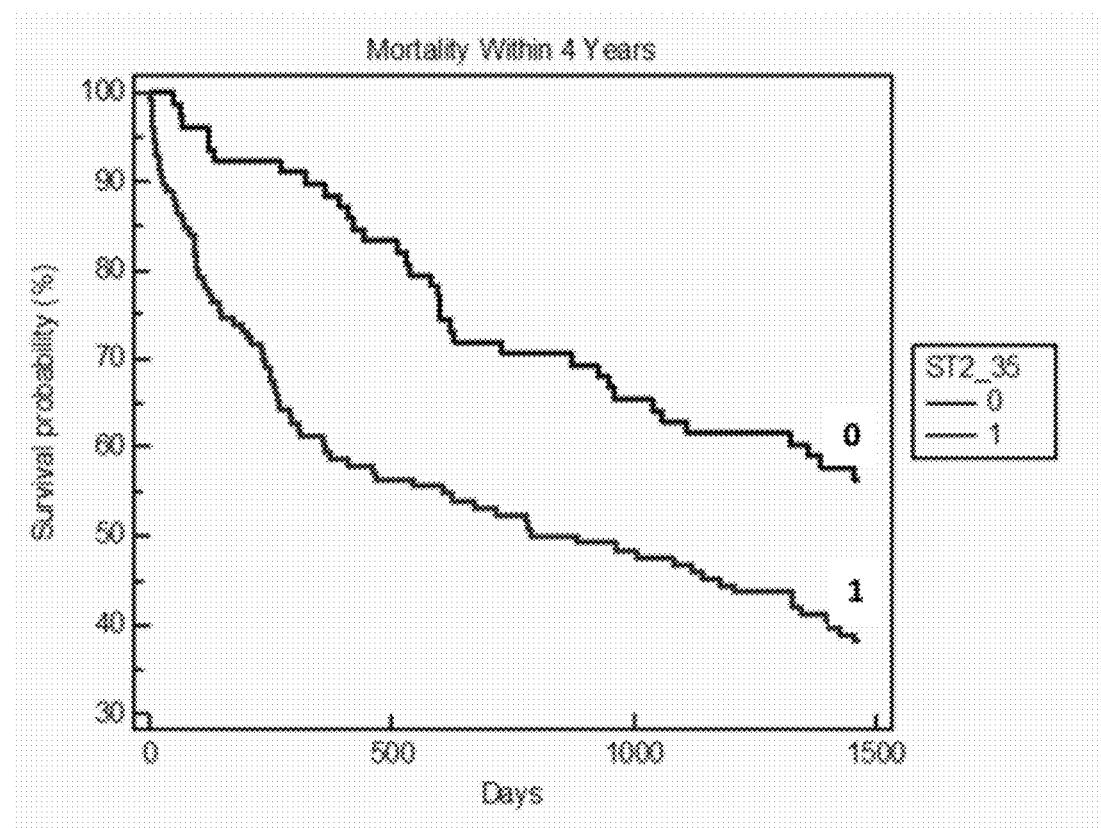

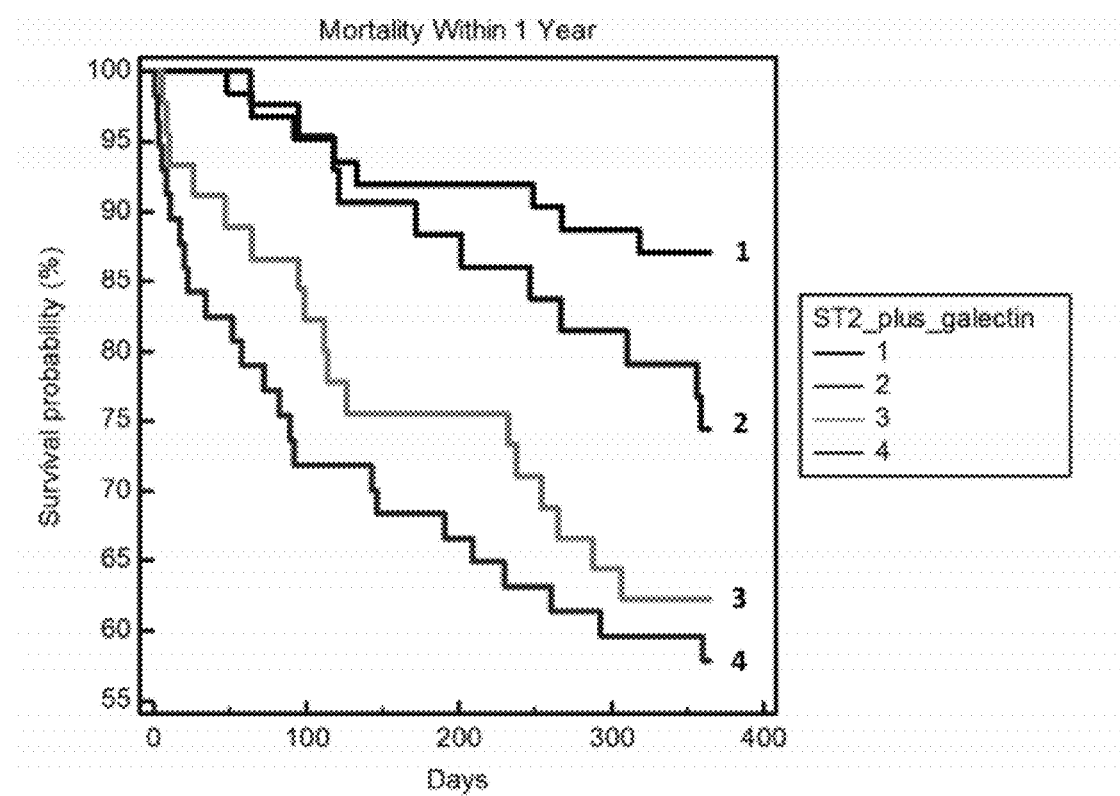
Figure 3: K-M Analysis of ST2 plus Galectin-3
4=both ≥median, 3=ST2≥median, galectin-3<median, 2=ST2<median, galectin-3≥median, 1=both <median

SEQUENCE LISTING

```
<160> NUMBER OF SEQ ID NOS: 6

<210> SEQ ID NO 1
<211> LENGTH: 328
<212> TYPE: PRT
<213> ORGANISM: Homo Sapiens

<400> SEQUENCE: 1

Met Gly Phe Trp Ile Leu Ala Ile Leu Thr Ile Leu Met Tyr Ser Thr
1               5                   10                  15

Ala Ala Lys Phe Ser Lys Gln Ser Trp Gly Leu Glu Asn Glu Ala Leu
            20                  25                  30

Ile Val Arg Cys Pro Arg Gln Gly Lys Pro Ser Tyr Thr Val Asp Trp
```

```
                    35                  40                  45
Tyr Tyr Ser Gln Thr Asn Lys Ser Ile Pro Thr Gln Glu Arg Asn Arg
 50                  55                  60

Val Phe Ala Ser Gly Gln Leu Leu Lys Phe Leu Pro Ala Ala Val Ala
 65                  70                  75                  80

Asp Ser Gly Ile Tyr Thr Cys Ile Val Arg Ser Pro Thr Phe Asn Arg
                 85                  90                  95

Thr Gly Tyr Ala Asn Val Thr Ile Tyr Lys Lys Gln Ser Asp Cys Asn
                100                 105                 110

Val Pro Asp Tyr Leu Met Tyr Ser Thr Val Ser Gly Ser Glu Lys Asn
                115                 120                 125

Ser Lys Ile Tyr Cys Pro Thr Ile Asp Leu Tyr Asn Trp Thr Ala Pro
130                 135                 140

Leu Glu Trp Phe Lys Asn Cys Gln Ala Leu Gln Gly Ser Arg Tyr Arg
145                 150                 155                 160

Ala His Lys Ser Phe Leu Val Ile Asp Asn Val Met Thr Glu Asp Ala
                165                 170                 175

Gly Asp Tyr Thr Cys Lys Phe Ile His Asn Glu Asn Gly Ala Asn Tyr
                180                 185                 190

Ser Val Thr Ala Thr Arg Ser Phe Thr Val Lys Asp Glu Gln Gly Phe
                195                 200                 205

Ser Leu Phe Pro Val Ile Gly Ala Pro Ala Gln Asn Glu Ile Lys Glu
                210                 215                 220

Val Glu Ile Gly Lys Asn Ala Asn Leu Thr Cys Ser Ala Cys Phe Gly
225                 230                 235                 240

Lys Gly Thr Gln Phe Leu Ala Ala Val Leu Trp Gln Leu Asn Gly Thr
                245                 250                 255

Lys Ile Thr Asp Phe Gly Glu Pro Arg Ile Gln Gln Glu Glu Gly Gln
                260                 265                 270

Asn Gln Ser Phe Ser Asn Gly Leu Ala Cys Leu Asp Met Val Leu Arg
                275                 280                 285

Ile Ala Asp Val Lys Glu Glu Asp Leu Leu Leu Gln Tyr Asp Cys Leu
290                 295                 300

Ala Leu Asn Leu His Gly Leu Arg Arg His Thr Val Arg Leu Ser Arg
305                 310                 315                 320

Lys Asn Pro Ser Lys Glu Cys Phe
                325

<210> SEQ ID NO 2
<211> LENGTH: 2542
<212> TYPE: DNA
<213> ORGANISM: Homo sapiens

<400> SEQUENCE: 2
gaggagggac ctacaaagac tggaaactat tcttagctcc gtcactgact ccaagttcat    60
cccctctgtc tttcagtttg gttgagatat aggctactct tcccaactca gtcttgaaga   120
gtatcaccaa ctgcctcatg tgtggtgacc ttcactgtcg tatgccagtg actcatctgg   180
agtaatctca caacgagtt accaatactt gctcttgatt gataaacaga atggggtttt   240
ggatcttagc aattctcaca attctcatgt attccacagc agcaaagttt agtaaacaat   300
catggggcct ggaaaatgag gctttaattg taagatgtcc tagacaagga aaacctagtt   360
acaccgtgga ttggtattac tcacaaacaa acaaaagtat tcccactcag gaaagaaatc   420
gtgtgtttgc ctcaggccaa cttctgaagt ttctaccagc tgcagttgct gattctggta   480
```

```
tttatacctg tattgtcaga agtcccacat tcaataggac tggatatgcg aatgtcacca    540
tatataaaaa acaatcagat tgcaatgttc cagattattt gatgtattca acagtatctg    600
gatcagaaaa aaattccaaa atttattgtc ctaccattga cctctacaac tggacagcac    660
ctcttgagtg gtttaagaat tgtcaggctc ttcaaggatc aaggtacagg gcgcacaagt    720
catttttggt cattgataat gtgatgactg aggacgcagg tgattacacc tgtaaattta    780
tacacaatga aaatggagcc aattatagtg tgacggcgac caggtccttc acggtcaagg    840
atgagcaagg cttttctctg tttccagtaa tcggagcccc tgcacaaaat gaaataaagg    900
aagtggaaat tggaaaaaac gcaaacctaa cttgctctgc ttgttttgga aaaggcactc    960
agttcttggc tgccgtcctg tggcagctta atggaacaaa aattacagac tttggtgaac   1020
caagaattca acaagaggaa gggcaaaatc aaagtttcag caatgggctg gcttgtctag   1080
acatggtttt aagaatagct gacgtgaagg aagaggattt attgctgcag tacgactgtc   1140
tggccctgaa tttgcatggc ttgagaaggc acaccgtaag actaagtagg aaaaatccaa   1200
gtaaggagtg tttctgagac tttgatcacc tgaactttct ctagcaagtg taagcagaat   1260
ggagtgtggt ccaagagat ccatcaagac aatgggaatg gcctgtgcca taaaatgtgc   1320
ttctcttctt cgggatgttg tttgctgtct gatctttgta gactgttcct gtttgctggg   1380
agcttctctg ctgcttaaat tgttcgtcct cccccactcc ctcctatcgt tggtttgtct   1440
agaacactca gctgcttctt tggtcatcct tgttttctaa ctttatgaac tccctctgtg   1500
tcactgtatg tgaaaggaaa tgcaccaaca accgtaaact gaacgtgttc ttttgtgctc   1560
ttttataact tgcattacat gttgtaagca tggtccgttc tataccttt tctggtcata   1620 atgaacactc attttgttag cgagggtggt aaagtgaaca aaaagggaa gtatcaaact   1680 actgccattt cagtgagaaa atcctagtgt ctactttata ataagacatt tgttaggcca   1740
ttcttgcatt gatataaaga aatacctgag actgggtgat ttatatgaaa agaggtttaa   1800
ttggctcaca gttctgcagg ctgtatggga agcatggcgg catctgcttc tggggacacc   1860
tcaggagctt tactcatggc agaaggcaaa gcaaaggcag gcacttcaca cagtaaaagc   1920
aggagcgaga gagaggtgcc acactgaaac agccagatct catgagaagt cactcactat   1980
tgcaaggaca gcatcaaaga gatggtgcta aaccattcat gatgaactca cccccatgat   2040
ccaatcacct cccaccaggc tccacctcga atactgggga ttaccattca gcatgagatt   2100
tgggcaggaa cacagaccca aaccatacca cacacattat cattgttaaa ctttgtaaag   2160
tatttaaggt acatggaaca cacgggaagt ctggtagctc agcccatttc tttattgcat   2220
ctgttattca ccatgtaatt caggtaccac gtattccagg gagcctttct tggccctcag   2280
tttgcagtat acacactttc caagtactct tgtagcatcc tgtttgtatc atagcactgg   2340
tcacattgcc ttacctaaat ctgtttgaca gtctgctcaa cacgactgca agctccatga   2400
gggcagggac atcatctctt ccatctttgg gtccttagtg caatacctgg cagctagcca   2460
gtgctcagct aaatatttgt tgactgaata aatgaatgca caaccaaaaa aaaaaaaaa   2520 aaaaaaaaaa aaaaaaaaaa aa                                           2542

<210> SEQ ID NO 3
<211> LENGTH: 200
<212> TYPE: PRT
<213> ORGANISM: Homo sapiens

<400> SEQUENCE: 3

Met Ala Asp Asn Phe Ser Leu His Asp Ala Leu Ser Gly Ser Gly Asn
1               5                   10                  15
```

```
Pro Asn Pro Gln Gly Trp Pro Gly Ala Trp Gly Asn Gln Pro Ala Gly
            20                  25                  30

Ala Gly Gly Tyr Pro Gly Ala Ser Tyr Pro Gly Ala Tyr Pro Gly Gln
        35                  40                  45

Ala Pro Pro Gly Ala Tyr Pro Gly Gln Ala Pro Pro Gly Ala Tyr Pro
 50                  55                  60

Gly Ala Pro Gly Ala Tyr Pro Gly Ala Pro Ala Pro Gly Val Tyr Pro
 65                  70                  75                  80

Gly Pro Pro Ser Gly Pro Gly Ala Tyr Pro Ser Ser Gly Gln Pro Ser
                85                  90                  95

Ala Thr Gly Ala Tyr Pro Ala Thr Gly Pro Tyr Gly Ala Pro Ala Gly
            100                 105                 110

Pro Leu Ile Val Pro Tyr Asn Leu Pro Leu Pro Gly Gly Val Val Pro
            115                 120                 125

Arg Met Leu Ile Thr Ile Leu Gly Thr Val Lys Pro Asn Ala Asn Arg
130                 135                 140

Ile Ala Leu Asp Phe Gln Arg Gly Asn Asp Val Ala Phe His Phe Asn
145                 150                 155                 160

Pro Arg Phe Asn Glu Asn Asn Arg Arg Val Ile Val Cys Thr Tyr Met
                165                 170                 175

Cys Lys Gly Phe Met Phe Thr Val Ser Glu Asn Phe Tyr Ile His Gln
            180                 185                 190

Tyr Pro Ser Cys Lys Ser Ser Thr
            195                 200

<210> SEQ ID NO 4
<211> LENGTH: 250
<212> TYPE: PRT
<213> ORGANISM: Homo sapiens

<400> SEQUENCE: 4

Met Ala Asp Asn Phe Ser Leu His Asp Ala Leu Ser Gly Ser Gly Asn
 1               5                  10                  15

Pro Asn Pro Gln Gly Trp Pro Gly Ala Trp Gly Asn Gln Pro Ala Gly
            20                  25                  30

Ala Gly Gly Tyr Pro Gly Ala Ser Tyr Pro Gly Ala Tyr Pro Gly Gln
        35                  40                  45

Ala Pro Pro Gly Ala Tyr Pro Gly Gln Ala Pro Pro Gly Ala Tyr Pro
 50                  55                  60

Gly Ala Pro Gly Ala Tyr Pro Gly Ala Pro Ala Pro Gly Val Tyr Pro
 65                  70                  75                  80

Gly Pro Pro Ser Gly Pro Gly Ala Tyr Pro Ser Ser Gly Gln Pro Ser
                85                  90                  95

Ala Thr Gly Ala Tyr Pro Ala Thr Gly Pro Tyr Gly Ala Pro Ala Gly
            100                 105                 110

Pro Leu Ile Val Pro Tyr Asn Leu Pro Leu Pro Gly Gly Val Val Pro
            115                 120                 125

Arg Met Leu Ile Thr Ile Leu Gly Thr Val Lys Pro Asn Ala Asn Arg
130                 135                 140

Ile Ala Leu Asp Phe Gln Arg Gly Asn Asp Val Ala Phe His Phe Asn
145                 150                 155                 160

Pro Arg Phe Asn Glu Asn Asn Arg Arg Val Ile Val Cys Asn Thr Lys
                165                 170                 175

Leu Asp Asn Asn Trp Gly Arg Glu Glu Arg Gln Ser Val Phe Pro Phe
            180                 185                 190
```

Glu Ser Gly Lys Pro Phe Lys Ile Gln Val Leu Val Glu Pro Asp His
        195                 200                 205

Phe Lys Val Ala Val Asn Asp Ala His Leu Leu Gln Tyr Asn His Arg
    210                 215                 220

Val Lys Lys Leu Asn Glu Ile Ser Lys Leu Gly Ile Ser Gly Asp Ile
225                 230                 235                 240

Asp Leu Thr Ser Ala Ser Tyr Thr Met Ile
            245                 250

<210> SEQ ID NO 5
<211> LENGTH: 744
<212> TYPE: DNA
<213> ORGANISM: Homo sapiens

<400> SEQUENCE: 5
gagtatttga ggctcggagc caccgccccg ccggcgcccg cagcacctcc tcgccagcag      60
ccgtccggag ccagccaacg agcggaaaat ggcagacaat ttttcgctcc atgatgcgtt     120
atctgggtct ggaaacccaa accctcaagg atggcctggc gcatggggga accagcctgc     180
tggggcaggg ggctacccag gggcttccta tcctggggcc taccccgggc aggcaccccc     240
aggggcttat cctggacagg cacctccagg cgcctaccct ggagcacctg gagcttatcc     300
cggagcacct gcacctggag tctacccagg gccaccagc ggccctgggg cctacccatc     360
ttctggacag ccaagtgcca ccggagccta ccctgccact ggcccctatg gcgcccctgc     420
tgggccactg attgtgcctt ataacctgcc tttgcctggg ggagtggtgc ctcgcatgct     480
gataacaatt ctgggcacgg tgaagcccaa tgcaaacaga attgctttag atttccaaag     540
agggaatgat gttgccttcc actttaaccc acgcttcaat gagaacaaca ggagagtcat     600
tgtttgcact acatgtgta aaggtttcat gttcactgtg agtgaaaatt tttacattca     660
tcaatatccc tcttgtaagt catctactta ataaatatta cagtgaatta cctgtctcaa     720
tatgtcaaaa aaaaaaaaaa aaaa                                            744

<210> SEQ ID NO 6
<211> LENGTH: 1017
<212> TYPE: DNA
<213> ORGANISM: Homo sapiens

<400> SEQUENCE: 6
gagtatttga ggctcggagc caccgccccg ccggcgcccg cagcacctcc tcgccagcag      60
ccgtccggag ccagccaacg agcggaaaat ggcagacaat ttttcgctcc atgatgcgtt     120
atctgggtct ggaaacccaa accctcaagg atggcctggc gcatggggga accagcctgc     180
tggggcaggg ggctacccag gggcttccta tcctggggcc taccccgggc aggcaccccc     240
aggggcttat cctggacagg cacctccagg cgcctaccct ggagcacctg gagcttatcc     300
cggagcacct gcacctggag tctacccagg gccaccagc ggccctgggg cctacccatc     360
ttctggacag ccaagtgcca ccggagccta ccctgccact ggcccctatg gcgcccctgc     420
tgggccactg attgtgcctt ataacctgcc tttgcctggg ggagtggtgc ctcgcatgct     480
gataacaatt ctgggcacgg tgaagcccaa tgcaaacaga attgctttag atttccaaag     540
agggaatgat gttgccttcc actttaaccc acgcttcaat gagaacaaca ggagagtcat     600
tgtttgcaat acaaagctgg ataataactg gggaagggaa gaaagacagt cggttttccc     660
atttgaaagt gggaaaccat tcaaaatca agtactggtt gaacctgacc acttcaaggt     720
tgcagtgaat gatgctcact gttgcagta caatcatcgg gttaaaaaac tcaatgaaat     780

-continued

```
cagcaaactg ggaatttctg gtgacataga cctcaccagt gcttcatata ccatgatata    840
atctgaaagg ggcagattaa aaaaaaaaaa agaatctaaa ccttacatgt gtaaaggttt    900
catgttcact gtgagtgaaa atttttacat tcatcaatat ccctcttgta agtcatctac    960
ttaataaata ttacagtgaa ttacctgtct caatatgtca aaaaaaaaaa aaaaaaa     1017
```

METHODS PREDICTING RISK OF AN ADVERSE CLINICAL OUTCOME

CROSS-REFERENCE TO RELATED APPLICATIONS

This application claims priority to U.S. provisional application 61/453,782, filed Mar. 17, 2011, the contents of each of which are incorporated herein by reference in their entirety.

TECHNICAL FIELD

Described herein are methods for the determining the risk of an adverse clinical outcome in a subject, selecting a therapeutic treatment for a subject, and selecting patients for participation in a clinical study.

SUMMARY

The present invention is based, at least in part, on the surprising discovery that the presence of an elevated level of galectin-3 or the presence of an elevated level of ST2 (also known as Interleukin 1 Receptor Like-1 (IL1RL1)) indicates a subject with an increased risk of an adverse clinical outcome (ACO), and the presence of both an elevated level of galectin-3 and an elevated level of ST2 indicates a subject with a greatly increased risk of an ACO. Thus, in some aspects, the methods described herein include determining the levels of galectin-3 and ST-2 in a subject, and, optionally, determining the levels of one or more (e.g., two, three, or four) of proANP, NT-pro-ANP, ANP, proBNP, NT-proBNP, BNP, troponin, CRP, creatinine, Blood Urea Nitrogen (BUN), liver function enzymes, albumin, and bacterial endotoxin in the subject. These methods can be used to determine the risk of an ACO, decide whether to discharge or to initiate, continue, or terminate treatment of a subject (e.g., treatment on an inpatient basis), select a subject for participation in a clinical study, or select a therapeutic treatment for a subject.

Accordingly, provided herein are methods for evaluating the risk of an ACO in a subject that include the steps of: (a) determining a level of ST2 in a biological sample (e.g., serum) from the subject, and (b) determining a level of galectin-3 in a biological sample (e.g., serum) from the subject, where the subject's levels of ST2 and galectin-3 relative to a reference levels of ST2 and galectin-3 indicate the subject's risk of an ACO. In some embodiments of these methods, the presence of an elevated level of ST2 or the presence of an elevated level of galectin-3 indicates an increased risk of an ACO, and the presence of both an elevated level of ST2 and an elevated level of galectin-3 indicates a greatly increased risk of an ACO. In some embodiments of these methods, the presence of both a non-elevated level of ST2 and a non-elevated level of galectin-3 indicates a reduced risk of an ACO. In some embodiments of these methods, the risk of an ACO is within 1 year or within 30 days.

Also provided are methods for deciding whether to discharge or initiate, terminate, or continue treating a subject (e.g., treating on an inpatient basis that include the steps of: (a) determining a level of ST2 in a biological sample (e.g., serum) from the subject, and (b) determining a level of galectin-3 in a biological sample (e.g., serum) from the subject, where the subject's levels of ST2 and galectin-3 relative to reference levels of ST2 and galectin-3 determine whether the subject should be discharged, receive continued treatment (e.g., treatment on an inpatient basis), or whether treatment should be initiated or terminated. In some embodiments of these methods, the presence of an elevated level of ST2 or the presence of an elevated level of galectin-3 indicates that the subject should receive continued treatment (e.g., treatment on an inpatient basis) or that treatment should be initiated, and the presence of both an elevated ST2 level and an elevated level of galectin-3 strongly indicates that the subject should receive continued treatment (e.g., treatment on an inpatient basis) or that treatment should be initiated. In some embodiments of these methods, the presence of both a non-elevated level of ST2 and a non-elevated level of galectin-3 indicates that the subject should be discharged, receive treatment on an outpatient basis, or that treatment should be terminated.

Also provided are methods of selecting a subject for participation in a clinical study that include the steps of: (a) determining a level of ST2 in a biological sample (e.g., serum) from the subject, and (b) determining a level of galectin-3 in a biological sample (e.g., serum) from the subject, and selecting the subject for participation in a clinical study if the subject's levels of ST2 and galectin-3 relative to reference levels of ST2 and galectin-3 indicate that the subject should be selected for participation in a clinical study. In some embodiments of these methods, the presence of an elevated level of ST2 or the presence of an elevated level of galectin-3 indicates that the subject should be selected for participation in a clinical study, and the presence of both an elevated level of ST2 and an elevated level of galectin-3 strongly indicates that the subject should be selected for participation in a clinical study. In some embodiments of these methods, the presence of a non-elevated level of ST2 and/or the presence of a non-elevated level of galectin-3 indicates that the subject should be excluded from participation in a clinical study.

Also provided are methods for selecting a therapeutic treatment for a subject that include the steps of: (a) determining a level of ST2 in a biological sample (e.g., serum) from the subject, and (b) determining a level of galectin-3 in a biological sample (e.g., serum) from the subject, where the subject's levels of ST2 and galectin-3 relative to reference levels of ST2 and galectin-3 are used to select a therapeutic treatment for the subject. In some embodiments of these methods, the presence of an elevated level of ST2 or the presence of an elevated level of galectin-3 is used to select the therapeutic treatment for the subject, and the presence of both an elevated level of ST2 and an elevated level of galectin-3 is predominantly used to select the therapeutic treatment for the subject. In some embodiments of these methods, the presence of a non-elevated level of ST2 and/or the presence of a non-elevated level of galectin-3 is used to select the therapeutic treatment for the subject. The therapeutic treatment may be selected from the group of: nitrates, calcium channel blockers, diuretics, thrombolytic agents, digitalis, renin-angiotensin-aldosterone system (RAAS) modulating agents (e.g., beta-adrenergic blocking agents (e.g., alprenolol, bucindolol, carteolol, carvedilol, labetalol, nadolol, penbutolol, pindolol, propranolol, sotalol, timolol, cebutolol, atenolol, betaxolol, bisoprolol, celiprolol, esmolol, metoprolol, and nebivolol), angiotensin-converting enzyme inhibitors (e.g., benazepril, captopril, enalapril, fosinopril, lisinopril, moexipril, perindopril, quinapril, ramipril, and trandolapril), aldosterone antagonists (e.g., spironolactone, eplerenone, canrenone (canrenoate potassium), prorenone (prorenoate potassium), and mexrenone (mexrenoate potassium)), renin inhibitors (e.g., aliskiren, remikiren, and enalkiren), and angiotensin II receptor blockers (e.g., valsartan, telmisartan, losartan, irbesartan, and olmesartan)), and cholesterol-lowering agents (e.g., a statin).

In some embodiments of all of the methods described herein, the ACO may be rehospitalization, recurrence of one or more (e.g., two, three, or four) physical symptoms associated with a disease state, an increase in the severity of one or more (e.g., two, three, or four) physical symptoms associated with a disease state, an increase in the frequency of one or more (e.g., two, three, or four) physical symptoms associated with a disease state, mortality (e.g., mortality due to CVD), admission to a health care facility (e.g., a hospital or assisted care facility), or organ transplant (e.g., heart transplant). In some embodiments, the disease state may be angina, cardiovascular disease, and heart failure. In the above methods, the rehospitalization or admission may be for cardiovascular disease.

In any of the above aspects, the subject may have been diagnosed with a cardiac disease (e.g., heart failure, heart attack, coronary artery disease, cardiovascular disease, acute coronary syndrome, and angina), inflammation, stroke, renal failure, obesity, high cholesterol, and/or dyslipidemia. In some embodiments of the above methods, the subject may be undiagnosed, normal, or apparently healthy. In some examples of all of the above methods, the sample may be serum, blood, or plasma. In some examples of the above methods, the sample in step (a) and the sample in step (b) are obtained from the subject at the same time.

In any of the above aspects, the subject may have an elevated BMI, a BMI of 25-29, a BMI of ≥30, or renal insufficiency. In further examples of any of the above methods, the reference level of ST2 is a level of ST2 in a subject that does not have high risk cardiovascular disease; the reference level of ST2 is a threshold level of ST2; the reference level of galectin-3 is a level of galectin-3 in a subject that does not have high risk cardiovascular disease or does not have galectin-3 positive cardiovascular disease; or the reference level of galectin-3 is a level of galectin-3 before or after onset of one or more (e.g., two, three, four, or five) disease (e.g., cardiac disease (e.g., heart failure, coronary artery disease, cardiovascular disease, acute coronary syndrome, and angina), renal insufficiency, stroke, or hypertension) symptoms; before or after diagnosis with disease (e.g., cardiac disease (e.g., heart failure, coronary artery disease, cardiovascular disease, acute coronary syndrome, and angina), renal insufficiency, stroke, or hypertension); before or after therapeutic treatment for a disease ((e.g., cardiac disease (e.g., heart failure, coronary artery disease, cardiovascular disease, acute coronary syndrome, and angina), renal insufficiency, stroke, or hypertension); or at a different time point during therapeutic treatment (e.g., inpatient or outpatient treatment) for a disease (e.g., cardiac disease (e.g., heart failure, coronary artery disease, cardiovascular disease, acute coronary syndrome, and angina), renal insufficiency, stroke, or hypertension); or before and after a cardiac event (e.g., a myocardial infarction).

In some embodiments of all of the above methods, the method further includes determining the level of one or more (e.g., two, three, or four) additional markers in the subject (e.g., proANP, NT-proANP, ANP, proBNP, NT-proBNP, BNP, troponin, CRP, creatinine, Blood Urea Nitrogen (BUN), liver function enzymes, albumin, and bacterial endotoxin).

Also provided are kits containing an antibody that specifically binds to ST2, an antibody that specifically binds to galectin-3, and instructions for using the kit in any of the methods described herein.

By the term "adverse clinical outcome" or "ACO" is meant an increase (e.g., by at least one, two, three, or four) in the number of symptoms or the severity or frequency of one of more (e.g., two, three, four, or five) symptoms in a subject, death, or therapeutic treatment that is necessitated by the increase (e.g., by at least one, two, three, or four) in the number or the severity or frequency of one or more (e.g., two, three, four, or five) symptoms in a subject. Non-limiting examples of an ACO include rehospitalization, recurrence of one or more (e.g., two, three, four, or five) physical symptoms associated with a disease state (e.g., cardiovascular disease), an increase in the severity of one or more (e.g., two, three, four, or five) physical symptoms associated with a disease state, an increase in the frequency of one or more (e.g., two, three, four, or five) physical symptoms associated with a disease state, mortality (e.g., mortality from a cardiovascular disease), admission to a health care facility (e.g., a hospital or assisted care facility), or organ transplant (e.g., heart transplant). The symptoms may be associated with a specific disease state, such a cardiac disease (e.g., heart failure, heart attack, coronary artery disease, cardiovascular disease, acute coronary syndrome, and angina), inflammation, stroke, renal failure, obesity, high cholesterol, or dyslipidemia.

By the term "ST2" or "soluble ST2" is meant a soluble protein containing a sequence at least 90% identical (e.g., at least 95%, 96%, 97%, 98%, 99%, or 100% identical) to NCBI Accession No. NP_003847.2 (SEQ ID NO: 1) or a nucleic acid containing a sequence at least 90% identical (e.g., at least 95%, 96%, 97%, 98%, 99%, or 100% identical) to NCBI Accession No. NM_003856.2 (SEQ ID NO: 2).

By the term "galectin-3" or "gal-3" is meant a protein containing a sequence at least 90% identical (e.g., at least 95%, 96%, 97%, 98%, 99%, or 100% identical) to NCBI Accession No. NP_001170859 (SEQ ID NO: 3), a protein containing a sequence at least 90% identical (e.g., at least 95%, 96%, 97%, 98%, 99%, or 100% identical) to NCBI Accession No. NP_002297 (SEQ ID NO: 4), a nucleic acid containing a sequence at least 90% identical (e.g., at least 95%, 96%, 97%, 98%, 99%, or 100% identical) to NCBI Accession No. NM_001177388.1 (SEQ ID NO: 5), a nucleic acid containing a sequence at least 90% identical (e.g., at least 95%, 96%, 97%, 98%, 99%, or 100% identical) to NCBI Accession No. NM_002306.3 (SEQ ID NO: 6).

By the term "elevated" or "elevation" is meant a statistically significant difference (e.g., an increase of at least 5%, 10%, 20%, 25%, 35%, 40%, 45%, 50%, 55%, 60%, 65%, 70%, 75%, 80%, 85%, 90%, 95%, 100%, 120%, 140%, 160%, 180%, 200%, 220%, 240%, 260%, 280%, or 300% increase) in a determined or measured level (e.g., a galectin-3 or ST2 protein or nucleic acid level) compared to a reference level (e.g., a level of galectin-3 in a subject not having high risk CVD or not having galectin-3 positive cardiovascular disease, a threshold level of galectin-3, a level of ST2 in a subject not having CVD, and a threshold level of ST2). The reference level of ST2 or galectin-3 may be a protein or nucleic acid level. Additional reference levels of ST2 and galectin-3 are described herein.

By the term "health care facility" is meant a location were a subject may receive medical care from a health care professional (e.g., a nurse, a physician, or a physician's assistant). Non-limiting examples of health care facilities include hospitals, clinics, and assisted care facilities (e.g., a nursing home).

By the term "reference level" is meant a threshold level or a level in a control subject or control patient population. A reference level will depend on the assay performed and can be determined by one of ordinary skill in the art. A reference level may be a baseline level or a level in the same patient measured at an earlier or later point in time. Some non-limiting examples of reference levels of ST2 include the level of ST2 in a subject that: does not have high risk CVD, does not have renal failure, or has a BMI under 25. Additional control patient populations are described herein. Additional examples of reference levels of ST2 include threshold levels of ST2. Non-limiting examples of reference levels of ST2 are known in the art and are described herein.

In some embodiments, the ratio of two ST2 levels in a subject is compared to a reference level that is a ratio of ST2 levels measured in a subject (e.g., any of the control subjects described herein or the same subject), for example, a reference level may be a ratio of the levels of ST2 before and after onset of one or more (e.g., two, three, four, or five) disease (e.g., cardiac disease (e.g., heart failure, coronary artery disease, cardiovascular disease, acute coronary syndrome, and angina), renal insufficiency, stroke, or hypertension) symptoms; a ratio of the levels of ST2 before and after diagnosis with disease (e.g., cardiac disease (e.g., heart failure, coronary artery disease, cardiovascular disease, acute coronary syndrome, and angina), renal insufficiency, stroke, or hypertension); a ratio of the levels of ST2 before and after therapeutic treatment for a disease ((e.g., cardiac disease (e.g., heart failure, coronary artery disease, cardiovascular disease, acute coronary syndrome, and angina), renal insufficiency, stroke, or hypertension); a ratio of the ST2 levels at two different time points during therapeutic treatment (e.g., inpatient or outpatient treatment) for a disease (e.g., cardiac disease (e.g., heart failure, coronary artery disease, cardiovascular disease, acute coronary syndrome, and angina), renal insufficiency, stroke, or hypertension); or a ratio of the ST2 levels before and after a cardiac event (e.g., a myocardial infarction).

Non-limiting examples of reference levels of galectin-3 include the level of galectin-3 in a subject that: does not have high risk CVD, does not have galectin-3 positive cardiovascular disease, does not have renal failure, or has a BMI under 25. Further control patient populations and threshold levels for a galectin-3 control are described herein. Additional non-limiting examples of reference levels of galectin-3 include threshold levels of galectin-3. Non-limiting examples of reference levels of galectin-3 are known in the art and are described herein.

Additional examples of a reference level of galectin-3 is a level of galectin-3 before or after onset of one or more (e.g., two, three, four, or five) disease (e.g., cardiac disease (e.g., heart failure, coronary artery disease, cardiovascular disease, acute coronary syndrome, and angina), renal insufficiency, stroke, or hypertension) symptoms; a level of galectin-3 before or after diagnosis with disease (e.g., cardiac disease (e.g., heart failure, coronary artery disease, cardiovascular disease, acute coronary syndrome, and angina), renal insufficiency, stroke, or hypertension); a level of galectin-3 before or after therapeutic treatment for a disease ((e.g., cardiac disease (e.g., heart failure, coronary artery disease, cardiovascular disease, acute coronary syndrome, and angina), renal insufficiency, stroke, or hypertension); or a level of galectin-3 at a different time point during therapeutic treatment (e.g., inpatient or outpatient treatment) for a disease (e.g., cardiac disease (e.g., heart failure, coronary artery disease, cardiovascular disease, acute coronary syndrome, and angina), renal insufficiency, or hypertension); or before and after a cardiac event (e.g., a myocardial infarction).

In some embodiments, the ratio of two galectin-3 levels in a subject is compared to a reference level that is a ratio of galectin-3 levels measured in a subject (e.g., any of the control subjects described herein or the same subject), for example, a reference level may be a ratio of the levels of galectin-3 before and after onset of one or more (e.g., two, three, four, or five) disease (e.g., cardiac disease (e.g., heart failure, coronary artery disease, cardiovascular disease, acute coronary syndrome, and angina), renal insufficiency, stroke, or hypertension) symptoms; a ratio of the levels of galectin-3 before and after diagnosis with disease (e.g., cardiac disease (e.g., heart failure, coronary artery disease, cardiovascular disease, acute coronary syndrome, and angina), renal insufficiency, stroke, or hypertension); a ratio of the levels of galectin-3 before and after therapeutic treatment for a disease ((e.g., cardiac disease (e.g., heart failure, coronary artery disease, cardiovascular disease, acute coronary syndrome, and angina), renal insufficiency, stroke, or hypertension); a ratio of the galectin-3 levels at two different time points during therapeutic treatment (e.g., inpatient or outpatient treatment) for a disease (e.g., cardiac disease (e.g., heart failure, coronary artery disease, cardiovascular disease, acute coronary syndrome, and angina), renal insufficiency, stroke, or hypertension); or a ratio of the galectin-3 levels before and after a cardiac event (e.g., a myocardial infarction).

By the term "therapeutic treatment" or "treatment" is meant the administration of one or more (e.g., two, three, or four) pharmaceutical agents to a subject or the performance of a medical procedure on the body of a subject (e.g., surgery, such as organ transplant or heart surgery). Non-limiting examples of pharmaceutical agents that may be administered to a subject include nitrates, calcium channel blockers, diuretics, thrombolytic agents, digitalis, renin-angiotensin-aldosterone system (RAAS) modulating agents (e.g., beta-adrenergic blocking agents, angiotensin-converting enzyme inhibitors, aldosterone antagonists, renin inhibitors, and angiotensin II receptor blockers), and cholesterol-lowering agents (e.g., a statin). The term therapeutic treatment also include an adjustment (e.g., increase or decrease) in the dose or frequency of one or more (e.g., two, three, or four) pharmaceutical agents that a subject may be taking, the administration of one or more (e.g., two, three, or four) new pharmaceutical agents to the subject, or the removal of one or more (e.g., two, three, or four) pharmaceutical agents from the subject's treatment plan.

As used herein, a "subject" is a mammal, e.g., a human. In all embodiments, human nucleic acids, human polypeptides, and human subjects can be used.

As used herein, a "biological sample" includes one or more of blood, serum, plasma, urine, and body tissue. In some embodiments, a sample is a serum or blood sample.

By the term "disease state" is meant the manifestation of one or more (e.g., at least two, three, four, or five) symptoms in a subject that indicate either an abnormal decrease in the viability and/or biological activity of one or more (e.g., at least two, three, four, or five) tissues in the body of the subject. Non-limiting examples of disease states in a subject include a cardiac disease (e.g., heart failure, heart attack, coronary artery disease, cardiovascular disease, acute coronary syndrome, and angina), inflammation, stroke, renal failure, obesity, high cholesterol, and dyslipidemia.

By the phrase "physical symptoms associated with a disease state" is meant the one or more (e.g., at least two, three, or four) symptoms that are manifested by a subject having a particular disease state. Physical symptoms associated with several disease states are known in the art by medical health professionals (e.g., physicians). Non-limiting examples of physical symptoms associated with a cardiac disease (e.g., heart failure, coronary artery disease, cardiovascular disease, acute coronary syndrome, and angina) include shortness of breath, heart palpitations, increased heart rate, weakness, dizziness, nausea, sweating, chest discomfort or pressure, chest pain, arm pain, fullness, indigestion, sweating, wheezing, sleep apnea, or anxiety.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

The details of one or more embodiments of the invention are set forth in the accompanying drawings and the description below. Other features, objects, and advantages of the invention will be apparent from the description and drawings, and from the claims.

DESCRIPTION OF DRAWINGS

FIG. 1 is two graphs depicting the data of a galectin-3 Kaplan-Meier (K-M) analysis for 1 year (FIG. 1A) or 4 years (FIG. 1B), which show the survival probability of subjects having low (below galectin-3 median level, 0) or elevated levels of galectin-3 (greater than or equal to galectin-3 median level, 1).

FIGS. 2A and 2B, together, are two graphs depicting the data of ST2 K-M analysis for 1 year (FIG. 2A) or 4 years (FIG. 2B), which show the survival probability of subjects having low (below soluble ST2 median level, 0) or elevated levels of soluble ST2 (greater than or equal to soluble ST2 median level, 1).

FIG. 2C is a graph depicting the data of a soluble ST2 K-M analysis, which shows the survival probability of subjects having low (below 35 ng/mL, 0) or elevated levels of soluble ST2 (greater than or equal to 35 ng/mL, 1).

FIG. 3 is a graph depicting the data from a soluble ST2 plus galectin-3 K-M analysis, which shows the survival probability of subjects with both soluble ST2 and galectin-3 levels below median level (1), subjects with a soluble ST2 level below median level and a galectin-3 level greater than or equal to median level (2), subjects with a soluble ST2 level greater than or equal to soluble ST2 median level and a galectin-3 level below galectin-3 median level (3), and subjects with a soluble ST2 level greater than or equal to median soluble ST2 levels and a galectin-3 level greater than or equal to galectin-3 median level (4).

DETAILED DESCRIPTION

Provided are methods for evaluating the risk of an ACO in a subject (e.g., a human), deciding whether to initiate, terminate, or continue treating a subject (e.g., treating on an inpatient basis), selecting a subject (e.g., a human) for participation in a clinical study, and selecting a subject (e.g., a human) for therapeutic treatment including the steps of determining (e.g., by measuring or assaying) a level of ST2 in a biological sample from the subject and determining (e.g., by measuring or assaying) a level of galectin-3 in a biological sample from the subject. Kits for performing these methods are also provided.

Galectin-3

Galectin-3 is a member of the galectin family, which consists of animal lectins that bind β-galactosides. Non-limiting examples of galectin-3 protein include a proteins containing a sequence at least 90% identical (e.g., at least 95%, 96%, 97%, 98%, 99%, or 100% identical) to the sequence of NCBI Accession Nos. NP_001170859 or NP_002297. Non-limiting examples of galectin-3 nucleic acids include nucleic acids containing a sequence at least 90% identical (e.g., at least 95%, 96%, 97%, 98%, 99%, or 100% identical) to the sequence of NCBI Accession Nos. NM_001177399.1 or NM_002306.3.

Recently, a role for galectin-3 in the pathophysiology of heart failure has been suggested (Sharma et al., Circulation 110:3121-3128 (2004)). It was observed that galectin-3 is specifically upregulated in decompensated heart failure compared with compensated heart failure in animal models of heart failure. Galectin-3 has recently been proposed as a useful biomarker involved in the pathophysiology of heart failure (de Boer et al., Eur. J. Heart Failure 11:811-817 (2009)). Galectin-3 is widely distributed throughout the body, including expression in heart, brain, and vessels (Yang et al., Expert Rev. Mol. Med. 13:e17-e39 (2008)). Specifically, secretion of galectin-3 is associated with activation of fibroblasts and fibrosis (Yang et al., supra).

Heart failure (HF) is a large medical and epidemiological problem, and recent studies, both in acute and chronic HF, indicate that it is associated with a high morbidity and mortality (Jessup et al., Circulation 48:1217-1224 (2009)). Early identification of high-risk patients may favorably affect outcome and biomarkers are increasingly being recognized to have important clinical value in this respect (Jessup et al., supra).

The first clinical study that evaluated the potential role of galectin-3 as a plasma biomarker in acute heart failure was published by van Kimmenade et al. (J. Am. Coll. Cardiol. 48:1217-1224 (2006)). In this study, 599 acutely dyspneic subjects were evaluated with the goal to establish the usefulness of N-terminal prohormone brain natriuretic peptide (NT-proBNP), galectin-3, and apelin in diagnosing heart failure and predicting outcome. A blood sample was collected at baseline, and NT-proBNP, galectin-3, and apelin were measured in that sample. A total of 209 patients in this cohort were diagnosed with heart failure. In this analysis, galectin-3 was not significant for diagnosis of heart failure but was significant for prognosis in patients with heart failure. For predicting short-term prognosis (60 days, primary end-point all-cause mortality [n=17]), galectin-3 was the most powerful predictor when compared to NT-proBNP and apelin: an AUC for galectin-3 of 0.74 (P=0.0001) and an AUC for NT-proBNP of 0.67 (P=0.009), with the difference being borderline significant (P=0.05). In multivariate analysis, galectin-3 was the strongest predictor for death within a 60 day follow up period. Nevertheless, this study provides strong support for the exploration of galectin-3 as a biomarker that may predict prognosis, whereas its usefulness in detecting heart failure or adding incremental value (over currently used clinical correlates and NT-proBNP) in the diagnostic work-up of heart failure remains unclear.

A larger study in patients with chronic heart failure (n=232), showed that galectin-3 predicts long-term outcome (mean follow-up, 3.4 y; HR, 1.95; 95% CI, 1.24-3.09; P=0.004) (Lok et al., Clin. Res. Cardiol. 99:323-328 (2010)). Because not many other biomarkers of heart failure were measured, it is impossible to value the precise role of galectin-3 in this cohort from this study.

Determining the level of galectin-3 in a subject typically includes obtaining a biological sample, e.g., plasma, serum, or blood, from the subject. In some embodiments, levels of galectin-3 in the sample can be determined by measuring levels of polypeptide using methods known in the art and/or described herein, e.g., immunoassays, such as enzyme-linked immunosorbent assays (ELISA). One exemplary ELISA kit that is commercial available is the galectin-3 ELISA kit available from EMD Chemicals. Alternatively, levels of galectin-3 mRNA can be measured, again using methods known in the art and/or described herein, e.g., by quantitative PCR or Northern blotting analysis.

For example, a method as described herein, e.g., evaluating the risk of an ACO in a subject, can include contacting a sample from a subject, e.g., a sample including blood, serum, or plasma, with a binding composition (e.g., an antibody or oligonucleotide probe) that specifically binds to a polypeptide or nucleic acid of galectin-3. The methods can also include contacting a sample from a control subject, normal subject, or normal tissue or fluid from the test subject, with the binding composition, e.g., to provide a reference level of galectin-3.

An antibody that "binds specifically to" an antigen, binds preferentially to the antigen in a sample containing other proteins. The term "antibody" as used herein refers to an immunoglobulin molecule or immunologically active portion thereof, i.e., an antigen-binding portion. Examples of immunologically active portions of immunoglobulin molecules include F(ab) and F(ab')2 fragments which can be generated by treating the antibody with an enzyme such as pepsin. The antibody can be polyclonal, monoclonal, recombinant, e.g., a chimeric or humanized, fully human, non-human, e.g., murine, monospecific, or single chain antibody. In some embodiments it has effector function and can fix complement. For the measurement of ST2, as further described below, an antibody produced from the hybridoma deposited at American Type Culture Collection and designated by Patent Deposit Designation PTA-10432 may be used.

An "oligonucleotide probe" (also referred to simply as a "probe") is a nucleic acid that is at least 10, and less than 200 (typically less than about 100 or 50) base pairs in length. A probe that "binds specifically to" a target nucleic acid hybridizes to the target under high stringency conditions. As used herein, the term "hybridizes under high stringency conditions" describes conditions for hybridization and washing. As used herein, high stringency conditions are 0.5 M sodium phosphate, 7% SDS at 65° C., followed by one or more washes at 0.2×SSC, 1% SDS at 65° C. Methods for performing nucleic acid hybridization assays are known to those skilled in the art and can be found in Current Protocols in Molecular Biology, John Wiley & Sons, N.Y. (1989), 6.3.1-6.3.6.

Detection can be facilitated by coupling (e.g., physically linking) the antibody or probe to a detectable substance (e.g., antibody labeling). Examples of detectable substances include various enzymes, prosthetic groups, fluorescent materials, luminescent materials, bioluminescent materials, and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride, quantum dots, or phycoerythrin; an example of a luminescent material includes luminol; examples of bioluminescent materials include luciferase, luciferin, and aequorin, and examples of suitable radioactive material include $^{125}I$, $^{131}I$, $^{35}S$, or $^{3}H$.

Diagnostic assays can be used with biological matrices such as live cells, cell extracts, cell lysates, fixed cells, cell cultures, bodily fluids, or forensic samples. Conjugated antibodies useful for diagnostic or kit purposes, include antibodies coupled to dyes, isotopes, enzymes, and metals, see, e.g., Le Doussal et al., New Engl. J. Med. 146:169-175 (1991); Gibellini et al., J. Immunol. 160:3891-3898 (1998); Hsing and Bishop, New Engl. J. Med. 162:2804-2811 (1999); and Everts et al., New Engl. J. Med. 168:883-889 (2002). Various assay formats exist, such as radioimmunoassays (RIA), enzyme-linked immunosorbent assay (ELISA), and lab on a chip (U.S. Pat. Nos. 6,176,962 and 6,517,234).

Known techniques in biochemistry and molecular biology can be used in the methods described herein (see, e.g., Maniatis et al., Molecular Cloning, A Laboratory Manual, Cold Spring Harbor Laboratory Press, Cold Spring Harbor, N.Y. (1982); Sambrook and Russell, Molecular Cloning, 3rd ed., Cold Spring Harbor Laboratory Press, Cold Spring Harbor, N.Y. (2001); Wu, Recombinant DNA, Vol. 217, Academic Press, San Diego, Calif. (1993); and Ausbel et al., Current Protocols in Molecular Biology, Vols. 1-4, John Wiley and Sons, Inc. New York, N.Y. (2001)).

Once a level of galectin-3 in a subject or sample has been determined, the level can be compared to a reference level. In some embodiments, e.g., where the level of galectin-3 is determined using an ELISA, the reference level will represent a threshold level, above which the subject is identified as having an increased risk of an ACO, is selected for continued treatment on an inpatient basis, is selected for participation in a clinical study, or is selected for therapeutic treatment (as described herein). The reference level chosen may depend on the methodology (e.g., the particular antibody or ELISA kit) used to measure the levels of galectin-3.

Non-limiting threshold levels of galectin-3 may represent the median level of galectin-3 in particular patient populations, e.g., subjects with a BMI of less than 25, subjects with normal renal function, subjects without high risk cardiovascular disease, subjects with a BMI between 25 and 30, subjects with a BMI greater than 30, subjects with an elevated BMI, subjects with renal insufficiency, healthy men, healthy women, and healthy children.

As noted above, a threshold level of galectin-3 may vary depending on the methodology used to measure the levels of galectin-3. For example, a threshold level of galectin-3 measured using the ELISA kit from Bender Medsystems, Vienna, Austria may be between 1.0 to 3.0 ng/mL, 2.0 to 4.0 ng/mL. 3.0 to 5.0 ng/mL, 4.0 to 6.0 ng/mL, 5.0 to 7.0 ng/mL, 6.0 to 8.0 ng/mL, 7.0 to 9.0 ng/mL, 1.0 to 5.0 ng/mL, 5.0 to 9.0 ng/mL, 7.0 to 11.0 ng/mL, or 9.0 to 13.0 ng/mL. Additional non-limiting examples of galectin-3 threshold levels include: 1.0 ng/mL, 1.1 ng/mL, 1.2 ng/mL, 1.3 ng/mL, 1.4 ng/mL, 1.5 ng/mL, 1.6 ng/mL, 1.7 ng/mL, 1.8 ng/mL, 1.9 ng/mL, 2.0 ng/mL, 2.1 ng/mL, 2.2 ng/mL, 2.3 ng/mL, 2.4 ng/mL, 2.5 ng/mL, 2.6 ng/mL, 2.7 ng/nL, 2.8 ng/mL, 2.9 ng/mL, 3.0 ng/mL, 3.1 ng/mL, 3.2 ng/mL, 3.3 ng/mL, 3.4 ng/mL, 3.5 ng/mL, 3.6 ng/mL, 3.7 ng/mL, 3.8 ng/mL, 3.9 ng/mL, 4.0 ng/mL, 4.1 ng/mL, 4.2 ng/mL, 4.3 ng/mL, 4.4 ng/mL, 4.5 ng/mL, 4.6 ng/mL, 4.7 ng/mL, 5.0 ng/mL, 5.2 ng/mL, 5.4 ng/mL. 5.6 ng/mL, 5.8 ng/mL, 6.0 ng/mL, 6.2 ng/mL, 6.4 ng/mL, 6.6 ng/mL, 6.8 ng/mL, 7.0 ng/mL, 7.2 ng/mL, 7.4 ng/mL, 7.6 ng/mL, 7.8 ng/mL, 8.0 ng/mL, 8.2 ng/mL, 8.4 ng/mL, 8.6 ng/mL, 8.8 ng/mL, and 9.0 ng/mL.

A threshold level of galectin-3 measured using the ELISA kit from BG Medicine, Inc. include: greater than 25.9 ng/mL, 17.8 ng/mL to 25.9 ng/mL, less than 17.8 ng/mL, 9 ng/mL, 10.0 ng/mL, 11.0 ng/mL, 12.0 ng/mL, 13.0 ng/mL, 14.0 ng/mL, 15.0 ng/mL, 16.0 ng/mL, 17.0 ng/mL, 18.0 ng/mL, 19.0 ng/mL, 20 ng/mL, 21 ng/mL, 22 ng/mL, 23 ng/mL, 24 ng/mL, 25 ng/mL, and 26 ng/mL.

Additional threshold values are known (e.g., Sharma et al., Circulation 110:3121-3128, (2004) and de Boer et al., Eur. J. Heart Failure 11:811-817 (2009)) and can readily be determined by one skilled in the art. A threshold value of galectin-3 may reflect the level of galectin-3 just below the level of galectin-3 observed in a subject presenting with one or more disease phenotypes (e.g., presenting with one or more symptoms of a disease state, such as cardiac disease (e.g., heart failure, coronary artery disease, cardiovascular disease, acute coronary syndrome, and angina), renal insufficiency, stroke, and hypertension).

Additional examples of a reference level of galectin-3 is a level of galectin-3 before or after onset of one or more (e.g., two, three, four, or five) disease (e.g., cardiac disease (e.g., heart failure, coronary artery disease, cardiovascular disease, acute coronary syndrome, and angina), renal insufficiency, stroke, or hypertension) symptoms; a level of galectin-3 before or after diagnosis with disease (e.g., cardiac disease (e.g., heart failure, coronary artery disease, cardiovascular disease, acute coronary syndrome, and angina), renal insufficiency, stroke, or hypertension); a level of galectin-3 before or after therapeutic treatment for a disease ((e.g., cardiac disease (e.g., heart failure, coronary artery disease, cardiovascular disease, acute coronary syndrome, and angina), renal insufficiency, stroke, or hypertension); or a level of galectin-3 at a different time point during therapeutic treatment (e.g., inpatient or outpatient treatment) for a disease (e.g., cardiac disease (e.g., heart failure, coronary artery disease, cardiovascular disease, acute coronary syndrome, and angina), renal insufficiency, or hypertension); or before and after a cardiac event (e.g., a myocardial infarction).

In some embodiments, the level of galectin-3 is determined once, e.g., at presentation. In some embodiments, the level of galectin-3 is determined at one or more of 2, 4, 6, 8, 12, 18, and/or 24 hours, and/or 1-7 days after the onset of symptoms.

In some embodiments, the level of galectin-3 is determined more than once; in some embodiments, the higher measurement can be used. In embodiments where the level of galectin-3 is determined more than once, the highest level can be used, or the change in levels (e.g., a ratio of two levels of galectin-3) can be determined and used.

In some embodiments, the ratio of two galectin-3 levels in a subject is compared to a reference level that is a ratio of galectin-3 levels measured in a subject (e.g., any of the control subjects described herein or the same subject), for example, a reference level may be a ratio of the levels of galectin-3 before and after onset of one or more (e.g., two, three, four, or five) disease (e.g., cardiac disease (e.g., heart failure, coronary artery disease, cardiovascular disease, acute coronary syndrome, and angina), renal insufficiency, stroke, or hypertension) symptoms; a ratio of the levels of galectin-3 before and after diagnosis with disease (e.g., cardiac disease (e.g., heart failure, coronary artery disease, cardiovascular disease, acute coronary syndrome, and angina), renal insufficiency, stroke, or hypertension); a ratio of the levels of galectin-3 before and after therapeutic treatment for a disease ((e.g., cardiac disease (e.g., heart failure, coronary artery disease, cardiovascular disease, acute coronary syndrome, and angina), renal insufficiency, stroke, or hypertension); a ratio of the galectin-3 levels at two different time points during therapeutic treatment (e.g., inpatient or outpatient treatment) for a disease (e.g., cardiac disease (e.g., heart failure, coronary artery disease, cardiovascular disease, acute coronary syndrome, and angina), renal insufficiency, stroke, or hypertension); or a ratio of the galectin-3 levels before and after a cardiac event (e.g., a myocardial infarction).

Levels of galectin-3 can also be determined multiple times to evaluate a subject's response to a treatment. For example, a level of galectin-3 taken after administration of a treatment, e.g., one or more doses or rounds of a treatment, can be compared to levels of galectin-3 before the treatment was initiated, e.g., a baseline level, or at an early time point in ongoing treatment. The change in galectin-3 levels would indicate whether the treatment was effective; e.g., a reduction in galectin-3 levels would indicate that the treatment was effective.

ST2

The ST2 gene is a member of the interleukin-1 receptor family, whose protein product exists both as a trans-membrane form, as well as a soluble receptor that is detectable in serum (Kieser et al., FEBS Lett. 372(2-3):189-93 (1995); Kumar et al., J. Biol. Chem. 270(46):27905-13 (1995); Yanagisawa et al., FEBS Lett. 302(1):51-3 (1992); Kuroiwa et al., Hybridoma 19(2):151-9 (2000)). ST2 was recently described to be markedly up-regulated in an experimental model of heart failure (Weinberg et al., Circulation 106(23): 2961-6 (2002)), and preliminary results suggest that ST2 concentrations may be elevated in those with chronic severe HF (Weinberg et al., Circulation 107(5):721-6 (2003)) as well as in those with acute myocardial infarction (MI) (Shimpo et al., Circulation 109(18):2186-90 (2004)).

The transmembrane form of ST2 is thought to play a role in modulating responses of T helper type 2 cells (Lohning et al., Proc. Natl. Acad. Sci. U.S.A. 95(12):6930-6935 (1998); Schmitz et al., Immunity 23(5):479-90 (2005)), and may play a role in development of tolerance in states of severe or chronic inflammation (Brint et al., Nat. Immunol. 5(4):373-9 (2004)), while the soluble form of ST2 is up-regulated in growth stimulated fibroblasts (Yanagisawa et al., 1992, supra). Experimental data suggest that the ST2 gene is markedly up-regulated in states of myocyte stretch (Weinberg et al., 2002, supra) in a manner analogous to the induction of the BNP gene (Bruneau et al., Cardiovasc. Res. 28(10):1519-25 (1994)).

Tominaga, FEBS Lett. 258:301-304 (1989), isolated murine genes that were specifically expressed by growth stimulation in BALB/c-3T3 cells; they termed one of these genes St2 (for Growth Stimulation-Expressed Gene 2). The St2 gene encodes two protein products: ST2 (IL1RL1), which is a soluble secreted form; and ST2L, a transmembrane receptor form that is very similar to the interleukin-1 receptors. The HUGO Nomenclature Committee designated the human homolog of ST2, the cloning of which was described in Tominaga et al., Biochim. Biophys. Acta. 1171:215-218 (1992), as Interleukin 1 Receptor-Like 1 (IL1RL1). The two terms are used interchangeably herein.

The mRNA sequence of the shorter, soluble isoform of human ST2 can be found at GenBank Acc. No. NM_003856.2, and the polypeptide sequence is at GenBank Acc. No. NP_003847.2; the mRNA sequence for the longer form of human ST2 is at GenBank Acc. No. NM_016232.4; the polypeptide sequence is at GenBank Acc. No. NP_057316.3. Additional information is available in the public databases at GeneID: 9173, MIM ID #601203, and UniGene No. Hs.66. In general, in the methods described herein, the soluble form of ST2 polypeptide is measured. Non-limiting examples of soluble ST2 protein include proteins containing a sequence at least 90% identical (e.g., at least 95%, 96%, 97%, 98%, 99%, or 100% identical) to the sequence of NCBI Accession Nos. NP_003847.2. Non-limiting examples of soluble ST2 nucleic acids include nucleic acids containing a sequence at least 90% identical (e.g., at least 95%, 96%, 97%, 98%, 99%, or 100% identical) to the sequence of NCBI Accession Nos. NM_003856.2.

Methods for detecting and measuring ST2 are known in the art, e.g., as described in U.S. Pat. Pub. Nos. 2003/0124624, 2004/0048286, and 2005/0130136, the entire contents of which are incorporated herein by reference. Kits for measuring ST2 polypeptide are also commercially available, e.g., the ST2 ELISA Kit manufactured by Medical & Biological Laboratories Co., Ltd. (MBL International Corp., Woburn, Mass.), no. 7638. In addition, devices for measuring ST2 and other biomarkers are described in U.S. Pat. Pub. No. 2005/0250156.

Levels of ST2 protein can also be measured using the antibodies produced from the hybridoma deposited at American Type Culture Collection and designated by Patent Deposit Designation PTA-10432, or any of the antibodies described in WO 2011/127412 and U.S. Patent Application Publication No. 2011/0256635 (herein incorporated by reference).

Elevated concentrations of ST2 are markedly prognostic for death, with a dramatic divergence in survival curves for those with elevated ST2 soon after presentation, regardless of the underlying diagnosis. As one example, there is a dramatic relationship between elevations of ST2 and the risk of mortality within four years following presentation with dyspnea. The relationship between ST2 and death in dyspneic patients was independent of diagnosis, and superseded all other biomarker predictors of mortality in this setting, including other markers of inflammation, myonecrosis, renal dysfunction, and most notably NT-proBNP, a marker recently described as having value for predicting death in this population (Januzzi et al., Arch. Intern. Med. 166(3):315-320 (2006)). Indeed, most of the mortality in the study was concentrated among subjects with elevated ST2 levels at presentation; however, the combination of elevated ST2 and NT-proBNP was associated with the highest rates of death within one year.

In some embodiments, the level of ST2 is determined once, e.g., at presentation. In some embodiments, the level of ST2 is determined at one or more of 2, 4, 6, 8, 12, 18, and/or 24 hours, and/or 1-7 days after the onset of symptoms.

In some embodiments, the level of ST2 is determined more than once; in some embodiments, the higher measurement can be used. In embodiments where the level of ST2 is determined more than once, the highest level can be used, or the change in levels (e.g., a ratio of two levels of ST2) can be determined and used.

Levels of ST2 can also be determined multiple times to evaluate a subject's response to a treatment. For example, a level of ST2 taken after administration of a treatment, e.g., one or more doses or rounds of a treatment, can be compared to levels of ST2 before the treatment was initiated, e.g., a baseline level, or at an early time point in ongoing treatment. The change in ST2 levels would indicate whether the treatment was effective; e.g., a reduction in ST2 levels would indicate that the treatment was effective.

In some embodiments, the methods include determining the identity of the nucleotide sequence at RefSNP ID: rs1041973.

Once a level of ST2 has been determined in a subject, the level may be compared to a reference level. In some embodiments, e.g., where the level of ST2 is determined using an ELISA, the reference level will represent a threshold level, above which the subject is identified as having an increased risk of an ACO, selected for continued treatment on an inpatient basis, selected for participation in a clinical study, or selected for therapeutic treatment (as described herein). The reference level chosen may depend on the methodology (e.g., the particular antibody or ELISA kit) used to measure the levels of ST2. Reference levels are known in the art and may readily be determined by one skilled in the art.

Non-limiting threshold levels of ST2 may represent the median level of ST2 in particular patient populations, e.g., subjects with a BMI of less than 25, subjects with normal renal function, subjects without cardiovascular disease, subjects with a BMI between 25 and 30, subjects with a BMI greater than 30, subjects with an elevated BMI, subjects with renal insufficiency, healthy men, healthy women, and healthy children. For example a threshold value for ST2 may fall within the range of about 1.0 to 10 ng/mL, 5.0 ng/mL to 10 ng/mL, about 10.0 ng/mL to 20.0 ng/mL, about 10.0 ng/mL to 15.0 ng/mL, about 15.0 ng/mL to 20.0 ng/mL, about 20.0 ng/ml to 40 ng/mL, about 20 ng/mL to 30 ng/mL, about 20 ng/mL to 25 ng/mL, about 25 ng/mL to 30 ng/mL, about 30 ng/mL to about 40 ng/mL, about 30 ng/mL to 35 ng/mL, about 35 ng/mL to 40 ng/mL, about 40 ng/mL to about 60 ng/mL, about 40 ng/mL to about 50 ng/mL, and about 50 ng/mL to about 60 ng/mL.

In some embodiments, the threshold value for ST2 in men and women may be any value listed in the Table 1. For example, the threshold value of ST2 in men may be 17.0 ng/mL, 18.0 ng/mL, 19.0 ng/mL, 20.0 ng/mL, 21.0 ng/mL, 22.0 ng/mL, 23.0 ng/mL, 24.0 ng/mL, 25.0 ng/mL, 26.0 ng/mL, 27.0 ng/mL, 28.0 ng/mL, 29.0 ng/mL, 30.0 ng/mL, 31.0 ng/mL, 32.0 ng/mL, 33.0 ng/mL, 34.0 ng/mL, 35.0 ng/mL, 36.0 ng/mL, 37.0 ng/mL, 38.0 ng/mL, 39.0 ng/mL, 40.0 ng/mL, 41.0 ng/mL, 42.0 ng/mL, 43.0 ng/mL, 44.0 ng/mL, 45.0 ng/mL, 46.0 ng/mL, 47.0 ng/mL, 48.0 ng/mL, 49.0 ng/mL, and 50.0 ng/mL. Exemplary threshold values of ST2 in women may be 12.0 ng/mL, 13.0 ng/mL, 14.0 ng/mL, 15.0 ng/mL, 16.0 ng/mL, 17.0 ng/mL, 18.0 ng/mL, 19.0 ng/mL, 20.0 ng/mL, 21.0 ng/mL, 22.0 ng/mL, 23.0 ng/mL, 24.0 ng/mL, 25.0 ng/mL, 26.0 ng/mL, 27.0 ng/mL, 28.0 ng/mL, 29.0 ng/mL, 30.0 ng/mL, 31.0 ng/mL, 32.0 ng/mL, 33.0 ng/mL, 34.0 ng/mL, 35.0 ng/mL, 36.0 ng/mL, 37.0 ng/mL, 38.0 ng/mL, 39.0 ng/mL, and 40.0 ng/mL.

TABLE 1

Serum ST2 Concentrations in Males and Females

| | ST2 (ng/mL) | | |
|---|---|---|---|
| Percentiles | Combined | Male | Female |
| 2.5 | 8.0 | 8.6 | 7.3 |
| 25 | 14.5 | 17.6 | 12.4 |
| 50 | 18.8 | 23.6 | 16.2 |
| 75 | 25.3 | 30.6 | 19.9 |
| 90 | 34.3 | 37.2 | 23.7 |
| 95 | 37.9 | 45.4 | 29.0 |
| 97.5 | 45.6 | 48.5 | 33.1 |
| 99 | 50.2 | 52.7 | 39.9 |

As noted above, a threshold level of ST2 may vary depending on the methodology used to measure the levels of ST2. For example, if an antibody produced from the hybridoma deposited at American Type Culture Collection, designated with Patent Deposit Deposition PTA-10432 is used to determine a ST2 level, non-limiting threshold values of ST2 may include: below 20 ng/mL, 5 ng/mL to 15 ng/mL, 5.0 ng/mL to 10 ng/mL, 10 ng/mL to 20 ng/mL, 10 ng/mL to 15 ng/mL, 14.5 ng/mL to 25.3 ng/mL, 15 ng/mL to 25 ng/mL, 15 ng/mL to 20 ng/mL, 18.0 ng/mL to 20.0 ng/mL, 18.1 ng/mL to 19.9 ng/mL, 20 ng/mL to 30 ng/mL, 20 ng/mL to 25 ng/mL, 25 ng/mL to 35 ng/mL, 25 ng/mL to 30 ng/mL, 30 ng/mL to 40 ng/mL, 30 ng/mL to 35 ng/mL, 35 ng/mL to 45 ng/mL, 35 ng/mL to 40 ng/mL, and 40 ng/mL to 45 ng/mL. Additional ST2 reference values that may be used when using the antibody produced from the hybridoma designated PTA-10432 is used to determine a ST2 level include: for women, 12.4 ng/mL to 19.9 ng/mL, 12.0 ng/mL to 20 ng/mL, 15.3 ng/mL to 17.4 ng/mL, 15.0 to 17.0 ng/mL, below 20 ng/mL, and below 18 ng/mL; and for men, less than 31.0 ng/mL, less than 26.0 ng/mL, 17.6 ng/mL to 30.6 ng/mL, 17.0 ng/mL to 30.0 ng/mL, 21.3 ng/mL to 25.1 ng/mL, and 21.0 ng/mL to 25.0 ng/mL. Additional non-limiting threshold values that may be used when a ST2 level is measured using the antibody produced from the hybridoma designated PTA-10432 include: 10 ng/mL, 11 ng/mL, 12 ng/mL, 13 ng/mL, 14 ng/mL, 15 ng/mL, 16 ng/mL, 17 ng/mL, 18 ng/mL, 19 ng/mL, 20 ng/mL, 21 ng/mL, 22 ng/mL, 23 ng/mL, 24 ng/mL, 25 ng/mL, 26 ng/mL, 27 ng/mL, 28 ng/mL, 29 ng/mL, 30 ng/mL, or 31 ng/mL.

In additional non-limiting examples, when a ST2 level is measured the ST2 ELISA Kit (MBL International Corp., Woburn, Mass.), the threshold levels of ST2 include: 0.1 ng/mL to 0.6 ng/mL, 0.2 ng/mL to 0.6 ng/mL, 0.2 ng/mL to 0.5 ng/mL, 0.3 ng/mL to 0.5 ng/mL, 0.2 ng/mL to 0.3 ng/mL, 0.3 ng/mL to 0.4 ng/mL, and 0.4 ng/mL to 0.5 ng/mL. Additional non-limiting threshold values when using the ST2 ELISA Kit (MBL International Corp.) to measure a ST2 level include: 0.17 ng/mL, 0.18 ng/mL, 0.19 ng/mL, 0.20 ng/mL, 0.21 ng/mL, 0.22 ng/mL, 0.23 ng/mL, 0.24 ng/mL, 0.25 ng/mL, 0.26 ng/mL, 0.27 ng/mL, 0.28 ng/mL, or 0.29 ng/mL of blood, serum, or plasma.

In some embodiments, the ratio of two ST2 levels in a subject is compared to a reference level that is a ratio of ST2 levels measured in a subject (e.g., any of the control subjects described herein or the same subject), for example, a reference level may be a ratio of the levels of ST2 before and after onset of one or more (e.g., two, three, four, or five) disease (e.g., cardiac disease (e.g., heart failure, coronary artery disease, cardiovascular disease, acute coronary syndrome, and angina), renal insufficiency, stroke, or hypertension) symptoms; a ratio of the levels of ST2 before and after diagnosis with disease (e.g., cardiac disease (e.g., heart failure, coronary artery disease, cardiovascular disease, acute coronary syndrome, and angina), renal insufficiency, stroke, or hypertension); a ratio of the levels of ST2 before and after therapeutic treatment for a disease ((e.g., cardiac disease (e.g., heart failure, coronary artery disease, cardiovascular disease, acute coronary syndrome, and angina), renal insufficiency, stroke, or hypertension); a ratio of the ST2 levels at two different time points during therapeutic treatment (e.g., inpatient or outpatient treatment) for a disease (e.g., cardiac disease (e.g., heart failure, coronary artery disease, cardiovascular disease, acute coronary syndrome, and angina), renal insufficiency, stroke, or hypertension); or a ratio of the ST2 levels before and after a cardiac event (e.g., a myocardial infarction).

Methods of Evaluating the Risk of ACO

Methods of evaluating the risk of an ACO in a subject are provided. In a clinical setting, patients may present with a combination of ambiguous symptoms, such that a physician or health care professional has difficulty in diagnosing the subject. In such situations, it is difficult for the physician to determine whether the subject has an increased risk of later experiencing an adverse clinical outcome. Provided are methods of evaluating the risk of an adverse clinical outcome in a subject requiring the steps of determining a level of ST2 in a biological sample from the subject and determining a level of galectin-2 in a biological sample from the subject.

An adverse clinical outcome (ACO) may be an increase (e.g., by one, two, three, or four) in the number, severity, or frequency of one or more (e.g., at least two, three, or four) symptoms in a subject, death, or treatment that is necessitated by the increase (e.g., by one, two, three, or four) in the number, severity, or frequency of one or more (e.g., at least two, three, or four) symptoms in a subject. An ACO may be the rehospitalization, recurrence of one or more (e.g., at least two, three, or four) physical symptoms associated with a disease state, an increase in the severity of one or more (e.g., at least two, three, or four) physical symptoms associated with a disease state, an increase in the frequency of one or more (e.g., at least two, three, or four) physical symptoms associated with a disease state, mortality, admission to a health care facility, organ transplant (e.g., heart transplant), or surgery (e.g., heart surgery). For example, the ACO may be an increase in the number, severity, duration, or frequency of one or more (e.g., at least two, three, or four) symptoms associated with angina, cardiovascular disease, or heart failure. For patients presenting with cardiovascular disease, the ACO may be, for example, rehospitalization or admission for cardiovascular disease or mortality.

The above methods may be performed on a subject presenting with one or more (e.g., at least two, three, or four) symptoms in a health care facility (e.g., hospital, such as in the emergency room). The method may be performed by a physician, a laboratory technician, a physician's assistant, or a nurse. A level of ST2 and galectin-3 may be measured in a biological sample from a patient within 14 days of the presentation of the patient to a health care facility (e.g., within 12 days, 10 days, 8 days, 7 days, 6 days, 5 days, 4 days, 3 days, 2 days, 36 hours, 24 hours, 20 hours, 16 hours, 12 hours, 10 hours, 8 hours, 6 hours, 4 hours, or 2 hours). The levels of ST2 and galectin-3 may also be measured in a biological sample from a subject that is already hospitalized or under medical supervision (e.g., periodic check-ups or in an assisted care facility). The levels of ST2 and galectin-3 may also be measured in a biological sample that has been previously collected from a subject.

Two different levels of ST2 and/or galectin-3 may be used to calculate a ratio which may then be compared to a reference level (e.g., any of the reference ratios described above). For example, a ratio of the levels of ST2 and/or galectin-3 before and after onset of one or more (e.g., two, three, four, or five) disease (e.g., cardiac disease (e.g., heart failure, coronary artery disease, cardiovascular disease, acute coronary syndrome, and angina), renal insufficiency, stroke, or hypertension) symptoms; a ratio of the levels of ST2 and/or galectin-3 before and after diagnosis with disease (e.g., cardiac disease (e.g., heart failure, coronary artery disease, cardiovascular disease, acute coronary syndrome, and angina), renal insufficiency, stroke, or hypertension); a ratio of the levels of ST2 and/or galectin-3 before and after therapeutic treatment for a disease ((e.g., cardiac disease (e.g., heart failure, coronary artery disease, cardiovascular disease, acute coronary syndrome, and angina), renal insufficiency, or hypertension); a ratio of the levels of ST2 and/or galectin-3 at two different time points during therapeutic treatment (e.g., inpatient or outpatient treatment) for a disease (e.g., cardiac disease (e.g., heart failure, coronary artery disease, cardiovascular disease, acute coronary syndrome, and angina), renal insufficiency, stroke, or hypertension); or a ratio of the ST2 and/or galectin-3 levels before and after a cardiac event (e.g., a myocardial infarction) may be determined and compared to a reference value.

The subject may have been previously diagnosed with a cardiac disease (e.g., heart failure, heart attack, coronary artery disease, cardiovascular disease, acute coronary syndrome, and angina), inflammation, stroke, renal failure, obesity, high cholesterol, and dyslipidemia. The subject may also not have been previously diagnosed as having a disease (e.g., a cardiac disease (e.g., heart failure, heart attack, coronary artery disease, cardiovascular disease, acute coronary syndrome, and angina), inflammation, stroke, renal failure, obesity, high cholesterol, and dyslipidemia). In some embodiments of the methods described herein, the subject may present with one or more ambiguous symptoms (e.g., shortness of breath, dizziness, discomfort, and nausea). The subject may have a BMI of between 25-29, a BMI of greater than or equal to 30, an elevated BMI, or have renal insufficiency.

The level of ST2 and galectin-3 may be measured in any biological sample obtained from the subject. Non-limiting biological samples that may be used in the methods described herein include blood, serum, and plasma. The biological sample used to measure ST2 and the biological sample used to measure galectin-3 may be gathered from the subject at the same time. The biological sample may be frozen or transported prior to determining the level of ST2 or galectin-3 present in the sample. Preferably, the biological sample used to determine the level of ST2 or galectin-3 is serum.

Following the determination of a level of ST2 in a biological sample from the subject and the determination of a level of galectin-3 in a biological sample from the subject, the risk of adverse clinical outcome is indicated by comparing the subject's levels of ST2 and galectin-3 to reference levels of ST2 and galectin-3. For example, the presence of an elevated level of ST2 (relative to a reference level of ST2) or the presence of an elevated level of galectin-3 (relative to a reference level of galectin-3) indicates an increased risk (e.g., an increased risk of at least 10%, 15%, 20%, 25%, 30%, 35%, 40%, 45%, 50%, 55%, 60%, 65%, 70%, 75%, 80%, 85%, 90%, 95%, 100%, 110%, 120%, 130%, 140%, 150%, 160%, 170%, 180%, 190%, or 200%) of an ACO. In some embodiments, the presence of both an elevated level of ST2 (relative to a reference level of ST2) and an elevated level of galectin-3 (relative to a reference level of galectin-3) indicates a greatly increased risk (e.g., an increased risk of at least 25%, 30%, 35%, 40%, 45%, 50%, 55%, 60%, 65%, 70%, 75%, 80%, 85%, 90%, 95%, 100%, 120%, 140%, 160%, 180%, 200%, 220%, 240%, 260%, 280%, or 300%) of an ACO. In some embodiments, a non-elevated level of ST2 and a non-elevated level of galectin-3 indicates a decreased (e.g., a decreased risk of at least 10%, 15%, 20%, 25%, 30%, 35%, 40%, 45%, 50%, 55%, 60%, 65%, 70%, 75%, or 80%) risk of an ACO.

In additional examples, the presence of an elevated ratio of ST2 levels (relative to a reference ratio of ST2 levels) or the presence of an elevated ratio of galectin-3 levels (relative to a reference ratio of galectin-3 levels) indicates an increased risk (e.g., an increased risk of at least 10%, 15%, 20%, 25%, 30%, 35%, 40%, 45%, 50%, 55%, 60%, 65%, 70%, 75%, 80%, 85%, 90%, 95%, 100%, 110%, 120%, 130%, 140%, 150%, 160%, 170%, 180%, 190%, or 200%) of an ACO. In some embodiments, the presence of both an elevated ratio of ST2 levels (relative to a reference ratio of ST2 levels) and an elevated ratio of galectin-3 levels (relative to a reference ratio of galectin-3 levels) indicates a greatly increased risk (e.g., an increased risk of at least 25%, 30%, 35%, 40%, 45%, 50%, 55%, 60%, 65%, 70%, 75%, 80%, 85%, 90%, 95%, 100%, 120%, 140%, 160%, 180%, 200%, 220%, 240%, 260%, 280%, or 300%) of an ACO. In some embodiments, a non-elevated ratio of ST2 levels (relative to a reference ratio of ST2 levels) and a non-elevated ratio of galectin-3 levels (relative to a reference ratio of galectin-3 levels) indicates a decreased risk (e.g., a decreased risk of at least 10%, 15%, 20%, 25%, 30%, 35%, 40%, 45%, 50%, 55%, 60%, 65%, 70%, 75%, or 80%) of an ACO.

Any of the above described reference levels for ST2 or galectin-3 may be used in these methods. Any of the above described techniques for determining the level of ST2 or galectin-3 may be used in these methods.

The above methods may be used to determine the risk of an ACO within 1 year and within 30 days of the time at which the biological sample was obtained from the subject.

Methods for Deciding to Discharge or Continue Treatment on an Inpatient Basis

Also provided are methods for deciding whether to discharge or initiate, terminate, or continue treating a subject on an inpatient basis including the steps of determining a level of ST2 in a biological sample, and determining a level of galectin-3 in a biological sample from the subject. This method may be performed by a health care professional (e.g., a physician, a physician's assistant, a nurse, or a laboratory technician).

Subjects often present to health care professionals with ambiguous symptoms (e.g., shortness of breath, dizziness, nausea, or discomfort) that are difficult to diagnose. Often a health care profession has to decide whether to discharge the subject or whether to continue to treat the subject on an inpatient basis (e.g., begin hospitalization, continue hospitalization, or admit to an assisted care facility). This method may be performed when a subject presents himself or herself to a health care professional at a health care facility. This method may also be performed on a subject who has already been admitted to a health care facility (e.g., a hospital or an assisted care facility).

The method may be performed on subjects that have cardiac disease (e.g., heart failure, coronary artery disease, cardiovascular disease, acute coronary syndrome, and angina), renal insufficiency, stroke, inflammation, or hypertension, or on subjects that present with one or more of the following symptoms: shortness of breath, heart palpitations, increased heart rate, weakness, dizziness, nausea, sweating, chest discomfort or pressure, chest pain, arm pain, fullness, indigestion, sweating, wheezing, sleep apnea, or anxiety. The method may also be performed on patients with a BMI of 25-30, a BMI of greater than 30, or an elevated BMI.

The level of ST2 and the level of galectin-3 may be measured in any of the biological samples described above. The levels of ST2 and galectin-3 may be measured using any of the methods described above and compared to any of the reference levels described above.

Following the determination of a level of ST2 in a biological sample from the subject and the determination of a level of galectin-3 in a biological sample from the subject, the subject's levels of ST2 and galectin-3 relative to reference levels of ST2 and galectin-3 is used to determine whether the subject should be discharged, should receive continued treatment (e.g., treatment on an inpatient basis) or whether treatment should be initiated or terminated. For example, the presence of an elevated level of ST2 (relative to a reference level of ST2) or the presence of an elevated level of galectin-3 (relative to a reference level of galectin-3) indicates that the subject should receive continued treatment (e.g., treatment on an inpatient basis) or that treatment should be initiated. In some embodiments of the methods described herein, the presence of both an elevated level of ST2 and an elevated level of galectin-3 (relative to control levels) strongly indicates that the subject should receive continued treatment (e.g., treatment on an inpatient basis) or that treatment should be initiated. In additional examples, the presence of a non-elevated level of ST2 (relative to a reference level of ST2) and the presence of a non-elevated level of galectin-3 (relative to a reference level of galectin-3) indicates that the subject should be discharged, receive treatment on an outpatient basis, or that treatment should be terminated.

Two different levels of ST2 and/or galectin-3 may be used to calculate a ratio which may then be compared to a reference level (e.g., a reference ratio as described above). For example, a ratio of the levels of ST2 and/or galectin-3 before and after onset of one or more (e.g., two, three, four, or five) disease (e.g., cardiac disease (e.g., heart failure, coronary artery disease, cardiovascular disease, acute coronary syndrome, and angina), renal insufficiency, stroke, or hypertension) symptoms; a ratio of the levels of ST2 and/or galectin-3 before and after diagnosis with disease (e.g., cardiac disease (e.g., heart failure, coronary artery disease, cardiovascular disease, acute coronary syndrome, and angina), renal insufficiency, stroke, or hypertension); a ratio of the levels of ST2 and/or galectin-3 before and after therapeutic treatment for a disease ((e.g., cardiac disease (e.g., heart failure, coronary artery disease, cardiovascular disease, acute coronary syndrome, and angina), renal insufficiency, stroke, or hypertension); a ratio of the levels of ST2 and/or galectin-3 at two different time points during therapeutic treatment (e.g., inpatient or outpatient treatment) for a disease (e.g., cardiac disease (e.g., heart failure, coronary artery disease, cardiovascular disease, acute coronary syndrome, and angina), renal insufficiency, stroke, or hypertension); or a ratio of the ST2 and/or galectin-3 levels before and after a cardiac event (e.g., a myocardial infarction) may be determined and compared to a reference value.

In additional examples, the presence of an elevated ratio of ST2 levels (relative to a reference ratio of ST2 levels) or the presence of an elevated ratio of galectin-3 levels (relative to a reference ratio of galectin-3 levels) indicates that the subject should receive continued treatment (e.g., treatment on an inpatient basis) or that treatment should be initiated. In some embodiments of the methods described herein, the presence of both an elevated ratio of ST2 levels (relative to a reference ratio of ST2 levels) and an elevated ratio of galectin-3 levels (relative to a reference ratio of galectin-3 levels) strongly indicates that the subject should receive continued treatment (e.g., treatment on an inpatient basis) or that treatment should be initiated. In some embodiments, a non-elevated ratio of ST2 levels (relative to a reference ratio of ST2 levels) and a non-elevated ratio of galectin-3 levels (relative to a reference ratio of galectin-3 levels) indicates that the subject should be discharged or that treatment should be terminated.

Continued treatment on an inpatient basis may mean new admission into a health care facility (e.g., a hospital or assisted care facility), continued admission in a health care facility (e.g., a hospital or assisted care facility), or frequent (e.g., daily, weekly, biweekly, or monthly) consistent visits to a health care center (e.g., a clinic or a hospital). The subject may receive one or more (e.g., at least two, three, four, or five) pharmaceutical agents during the continued treatment or may be tested periodically for changes in the levels of ST2 and/or galectin-3 in a biological sample from the subject. A decrease in a subject's ST2 and/or galectin-3 level relative to a reference sample (determined by subsequent testing) may later indicate that the subject may be discharged.

Methods for Selecting a Subject for Participation in a Clinical Study

Also provided are methods for selecting a subject for participation in a clinical study that include the steps of determining a level of ST2 in a biological sample in a subject and determining a level of galectin-3 in a biological sample in a subject.

Non-limiting examples of clinical studies include studies of cardiac disease (e.g., heart failure, heart attack, coronary artery disease, cardiovascular disease, acute coronary syndrome, and angina), inflammation, stroke, renal failure, obesity, high cholesterol, and dyslipidemia. The clinical studies may also be used to study the effect of treatment of one or more (e.g., two, three, or four) pharmaceutical agents (e.g., nitrates, calcium channel blockers, diuretics, thrombolytic agents, digitalis, renin-angiotensin-aldosterone system (RAAS) modulating agents (e.g., beta-adrenergic blocking agents, angiotensin-converting enzyme inhibitors, aldosterone antagonists, renin inhibitors, and angiotensin II receptor blockers), and cholesterol-lowering agents (e.g., a statin)) on a subject.

The clinical studies may be performed by health care professionals (e.g., physicians, physician's assistants, nurses, phlebotomists, or laboratory technicians) in a health care facility (e.g., a hospital, a clinic, or a research center). The biological samples may be obtained from subjects present with one or more (e.g., at least two, three, four, or five) symptoms of a disease state (e.g., cardiovascular disease, angina, or heart failure), subjects that are admitted in a hospital, or subjects who are asymptomatic.

The level of ST2 and the level of galectin-3 may be measured in any of the biological samples described above. The levels of ST2 and galectin-3 may be measured using any of the methods described above and compared to any of the reference levels described above.

Following the determination of a level of ST2 in a biological sample from the subject and the determination of a level of galectin-3 in a biological sample from the subject, a subject is selected for participation in a clinical study based on the comparison of subject's levels of ST2 and galectin-3 to reference levels of ST2 and galectin-3. For example, the subject is selected for participation in a clinical study if the subject has an elevated level of ST2 (relative to a reference level of ST2) or an elevated level of galectin-3 (relative to a reference level of galectin-3). In some embodiments of the methods described herein, the subject is strongly selected for participation in a clinical study if the subject has both an elevated level of ST2 (relative to a reference level of ST2) and an elevated level of galectin-3 (relative to a reference level of galectin-3). In some embodiments, the subject is excluded from participation in a clinical study if the subject has both a non-elevated level of ST2 (relative to a reference level of ST2) and a non-elevated level of galectin-3 (relative to a reference level of galectin-3).

In another embodiment, a subject with a level of galectin-3 that is lower than a reference level of galectin-3 (e.g., a subject having an elevated level of ST2 compared to a reference level and a decreased level of galectin-3 relative to a reference level) may be selected for participation in a clinical study (e.g., a study of the effect of one or more (e.g., at least two, three, or four) statins in a subject (e.g., a subject with a cardiac disease (e.g., heart failure, heart attack, coronary artery disease, cardiovascular disease, acute coronary syndrome, and angina), inflammation, stroke, renal failure, obesity, high cholesterol, and/or dyslipidemia).

As described above, two different levels of ST2 and/or galectin-3 may be used to calculate a ratio which may then be compared to a reference level (e.g., a reference ratio as described above). For example, a ratio of the levels of ST2 and/or galectin-3 before and after onset of one or more (e.g., two, three, four, or five) disease (e.g., a cardiac disease (e.g., heart failure, heart attack, coronary artery disease, cardiovascular disease, acute coronary syndrome, and angina), inflammation, stroke, renal failure, obesity, high cholesterol, and dyslipidemia), renal insufficiency, and hypertension) symptoms; a ratio of the levels of ST2 and/or galectin-3 before and after diagnosis with disease (e.g., a cardiac disease (e.g., heart failure, heart attack, coronary artery disease, cardiovascular disease, acute coronary syndrome, and angina), inflammation, stroke, renal failure, obesity, high cholesterol, and dyslipidemia); a ratio of the levels of ST2 and/or galectin-3 before and after therapeutic treatment for a disease (e.g., a cardiac disease (e.g., heart failure, heart attack, coronary artery disease, cardiovascular disease, acute coronary syndrome, and angina), inflammation, stroke, renal failure, obesity, high cholesterol, and dyslipidemia); a ratio of the levels of ST2 and/or galectin-3 at two different time points during therapeutic treatment (e.g., inpatient or outpatient treatment) for a disease (e.g., a cardiac disease (e.g., heart failure, heart attack, coronary artery disease, cardiovascular disease, acute coronary syndrome, and angina), inflammation, stroke, renal failure, obesity, high cholesterol, and dyslipidemia); or a ratio of the ST2 and/or galectin-3 levels before and after a cardiac event (e.g., a myocardial infarction) may be determined and compared to a reference value.

In some examples of the methods described herein, a subject is selected for participation in a clinical study if the subject has an elevated ratio of ST2 levels (relative to a reference ratio of ST2 levels) or an elevated ratio of galectin-3 levels (relative to a reference ratio of galectin-3 levels). In some examples of the methods described herein, a subject is strongly selected for participation in a clinical study if the subject has an elevated ratio of ST2 levels (relative to a reference ratio of ST2 levels) and an elevated ratio of galectin-3 levels (relative to a reference ratio of galectin-3 levels). In some embodiments, a subject is excluded from participation in a clinical study if the subject has a non-elevated ratio of ST2 levels (relative to a reference ratio of ST2 levels) and a non-elevated ratio of galectin-3 levels (relative to a reference level of galectin-3 levels).

Additional factors may further indicate that the subject should be included in a clinical study. These additional factors include prior diagnosis with cardiovascular disease, angina, heart attack, heart failure, renal failure, inflammation, or stroke, or presentation of one or more (e.g., two, three, or four) of the following symptoms: shortness of breath, heart palpitations, increased heart rate, weakness, dizziness, nausea, sweating, chest discomfort or pressure, chest pain, arm pain, fullness, indigestion, sweating, wheezing, sleep apnea, and anxiety. Additional factors include a BMI of 25-30, a BMI of greater than 30, an elevated BMI, or continued therapy on one or more (e.g., at least two, three, four, or five) pharmaceutical agents (e.g., nitrates, calcium channel blockers, diuretics, thrombolytic agents, digitalis, renin-angiotensin-aldosterone system (RAAS) modulating agents (e.g., beta-adrenergic blocking agents, angiotensin-converting enzyme inhibitors, aldosterone antagonists, renin inhibitors, and angiotensin II receptor blockers), and cholesterol-lowering agents (e.g., a statin)).

Methods for Selecting a Therapeutic Treatment for a Subject

Also provided are methods for selecting a treatment for a subject requiring the steps of determining a level of ST2 in a biological sample from the subject and determining a level of galectin-3 in a biological sample from the subject.

This method may be performed on subjects that present clinically (e.g., diagnosed) with one or more (e.g., at least two, three, four, or five) symptoms of a disease (e.g., a cardiac disease (e.g., heart failure, heart attack, coronary artery disease, cardiovascular disease, acute coronary syndrome, and angina), inflammation, stroke, renal failure, obesity, high cholesterol, and dyslipidemia). The method may also be performed on subjects that present with one or more (e.g., two, three, or four) of the following symptoms: shortness of breath, heart palpitations, increased heart rate, weakness, dizziness, nausea, sweating, chest discomfort or pressure, chest pain, arm pain, fullness, indigestion, sweating, wheezing, sleep apnea, and anxiety. The subject may have been previously diagnosed one or more (e.g., two, three, four, or five) of the following conditions: a cardiac disease (e.g., heart failure, heart attack, coronary artery disease, cardiovascular disease, acute coronary syndrome, and angina), inflammation, stroke, renal failure, obesity, high cholesterol, and dyslipidemia, or the subject may not have been previously diagnosed with a disease. The subject may have been previously admitted to a health care facility and previously discharged, or may be a patient admitted in a health care facility (e.g., hospital or assisted care facility). The methods may be performed by a health care professional (e.g., a physician, a physician's assistant, a nurse, or a laboratory technician) in a health care facility (e.g., a hospital, clinic, or assisted care facility).

The level of ST2 and the level of galectin-3 may be measured in any of the biological samples described above. The levels of ST2 and galectin-3 may be measured using any of the methods described above and compared to any of the reference levels described above.

Following the determination of a level of ST2 in a biological sample from the subject and the determination of a level of galectin-3 in a biological sample from the subject, the subject's levels of ST2 and galectin-3 relative to reference levels of ST2 and galectin-3 is used to select a treatment for the subject. For example, the presence of an elevated level of ST2 (relative to a reference level of ST2) or the presence of an elevated level of galectin-3 (relative to a reference level of galectin-3) is used to select a treatment for the subject. In some embodiments of the methods described herein, the presence of both an elevated level of ST2 and an elevated level of galectin-3 (relative to control levels) is predominantly (strongly) used to select the therapeutic treatment for the subject. In some embodiments of the methods described herein, the presence of both a non-elevated level of ST2 and a non-elevated level of galectin-3 (relative to control levels) is used to select a therapeutic treatment for the subject.

As described above, two different levels of ST2 and/or galectin-3 may be used to calculate a ratio which may then be compared to a reference level (e.g., a reference ratio as described above). For example, a ratio of the levels of ST2 and/or galectin-3 before and after onset of one or more (e.g., two, three, four, or five) disease (e.g., a cardiac disease (e.g., heart failure, heart attack, coronary artery disease, cardiovascular disease, acute coronary syndrome, and angina), inflammation, stroke, renal failure, obesity, high cholesterol, and dyslipidemia) symptoms; a ratio of the levels of ST2 and/or galectin-3 before and after diagnosis with disease (e.g., a cardiac disease (e.g., heart failure, heart attack, coronary artery disease, cardiovascular disease, acute coronary syndrome, and angina), inflammation, stroke, renal failure, obesity, high cholesterol, and dyslipidemia); a ratio of the levels of ST2 and/or galectin-3 before and after therapeutic treatment for a disease (e.g., a cardiac disease (e.g., heart failure, heart attack, coronary artery disease, cardiovascular disease, acute coronary syndrome, and angina), inflammation, stroke, renal failure, obesity, high cholesterol, and dyslipidemia); a ratio of the levels of ST2 and/or galectin-3 at two different time points during therapeutic treatment (e.g., inpatient or outpatient treatment) for a disease (e.g., a cardiac disease (e.g., heart failure, heart attack, coronary artery disease, cardiovascular disease, acute coronary syndrome, and angina), inflammation, stroke, renal failure, obesity, high cholesterol, and dyslipidemia); or a ratio of the ST2 and/or galectin-3 levels before and after a cardiac event (e.g., a myocardial infarction) may be determined and compared to a reference value.

In some examples of the methods described herein, the presence of an elevated ratio of ST2 levels (relative to a reference ratio of ST2 levels) or the presence of an elevated ratio of galectin-3 levels (relative to a reference ratio of galectin-3 levels) is used to select a treatment for a subject. In some examples of the methods described herein, the presence of both an elevated ratio of ST2 levels (relative to a reference ratio of ST2 levels) and an elevated ratio of galectin-3 levels (relative to a reference ratio of galectin-3 levels) is strongly used to select a treatment for a subject. In some embodiments, the presence of a non-elevated ratio of ST2 levels (relative to a reference ratio of ST2 levels) and the presence of a non-elevated ratio of galectin-3 levels (relative to a reference level of galectin-3 levels) is used to select a treatment for a subject.

Additional factors may further be used to select a therapeutic treatment for the subject. These additional factors include prior diagnosis with one or more (e.g., two, three, four, or five) of the following conditions: cardiovascular disease, angina, heart attack, heart failure, renal failure, inflammation, and stroke, and/or presentation of one or more (e.g., two, three, or four) of the following symptoms: shortness of breath, heart palpitations, increased heart rate, weakness, dizziness, nausea, sweating, chest discomfort or pressure, chest pain, arm pain, fullness, indigestion, sweating, wheezing, sleep apnea, or anxiety. Additional factors include a BMI of 25-30, a BMI of greater than 30, an elevated BMI, or continued therapy on one or more (e.g., at least two, three, four, or five) pharmaceutical agents (e.g., nitrates, calcium channel blockers, diuretics, thrombolytic agents, digitalis, renin-angiotensin-aldosterone system (RAAS) modulating agents (e.g., beta-adrenergic blocking agents, angiotensin-converting enzyme inhibitors, aldosterone antagonists, renin inhibitors, and angiotensin II receptor blockers), and cholesterol-lowering agents (e.g., a statin)). Examples of these pharmaceutical agents are well known in the art.

The therapeutic treatment may be the administration of one or more (e.g., two, three, or four) pharmaceutical agents to the subject and/or the performance of a medical procedure on the body of the subject (e.g., surgery, such as organ transplant or heart surgery). Non-limiting examples of pharmaceutical agents that may be administered to a subject include nitrates, calcium channel blockers, diuretics, thrombolytic agents, digitalis, renin-angiotensin-aldosterone system (RAAS) modulating agents (e.g., beta-adrenergic blocking agents, angiotensin-converting enzyme inhibitors, aldosterone antagonists, renin inhibitors, and angiotensin II receptor blockers), and cholesterol-lowering agents (e.g., a statin). In another example, the therapeutic treatment may be an adjustment (e.g., an increase or decrease) in the dose, duration, or frequency of one or more (e.g., at least two, three, or four) pharmaceutical agents that a subject may be taking, the administration of one or more (e.g., at least two, three, or four) new pharmaceutical agents to the subject, or the removal of one or more (e.g., at least two, three, or four) pharmaceutical agents from the subject's treatment plan.

These methods may be repeated over time (e.g., weekly, biweekly, monthly, once every two months, once every six months, once a year) to select a different therapeutic treatment for the subject.

Additional Markers

Some embodiments of all of the above methods, may further include determining the level of one or more (e.g., at least two, three, four, or four) additional markers in a biological sample from the subject. The additional markers may be selected from the group of: proANP, NT-proANP, ANP, proBNP, NT-proBNP, BNP, troponin, CRP, creatinine, Blood Urea Nitrogen (BUN), liver function enzymes, albumin, and bacterial endotoxin. The one or more additional markers can be measured in any of the biological samples described above. The presence of an increased level (e.g., at least 10%, 15%, 20%, 25%, 30%, 35%, 40%, 45%, 50%, 55%, 60%, 65%, 70%, 75%, 80%, 85%, 90%, 95%, 100%, 110%, 120%, 130%, 140%, 150%, 160%, 170%, 180%, 190%, 200%, 210%, 220%, 230%, 240%, 250%, 260%, 270%, 280%, 290%, or 300%) of one or more (e.g., at least two, three, or four) of proANP, NT-proANP, ANP, proBNP, NT-proBNP, BNP, troponin, CRP, creatinine, Blood Urea Nitrogen (BUN), liver function enzymes, albumin, and bacterial endotoxin in a subject compared to a reference level for each of these markers may further indicate that the subject has an increased risk of an ACO, the subject should receive continued treatment (e.g., treatment on an inpatient basis) or that treatment should be initiated or terminated, the subject should be selected for participation in a clinical study, or the subject should be selected for treatment. The reference levels of these additional markers may be a threshold value or may be the level of these markers in a patient population, e.g., subjects with a BMI of less than 25, subjects with normal renal function, subjects without cardiovascular disease, subjects with a BMI between 25 and 30, subjects with a BMI greater than 30, subject with an elevated BMI, subjects with renal insufficiency, healthy men, healthy women, and healthy children. Preferably, the above methods further include determining the level of BNP.

Methods for determining the levels of these additional markers are known in the art. Commercial kits for determining these additional markers are available.

Kits

Also provided are kits containing an antibody that specifically binds to ST2, an antibody that specifically binds to galectin-3, and instructions for using the kit (e.g., the antibodies in the kit) to perform any of the methods described herein. The antibody that specifically binds ST2 and the antibody that specifically binds to galectin-3 may be polyclonal, monoclonal, recombinant, e.g., a chimeric or humanized, fully human, non-human, e.g., murine, monospecific, or single chain antibody. Any of the kits described herein may also be provided as an ELISA assay (e.g., may further include one or more secondary antibodies and/or a substrate for detection). For example, any of the kits described herein may include an antibody produced from the hybridoma deposited at American Type Culture Collection and designated by Patent Deposit Designation PTA-10432. Additional examples of antibodies that specifically bind to ST2 are described in WO 2011/127412 and U.S. Patent Application Publication No. 2011/0256635 (herein incorporated by reference).

Any of the kits described herein may also include one or more (e.g., two, three, four, or five) additional antibodies for one or more (e.g., two, three, four, or five) additional markers selected from the group of: proANP, NT-proANP, ANP, proBNP, NT-proBNP, BNP, troponin, CRP, creatinine, liver function enzymes, albumin, and bacterial endotoxin. Antibodies for ST2, galectin-3, proANP, NT-proANP, ANP, proBNP, NT-proBNP, BNP, troponin, CRP, creatinine, liver function enzymes, albumin, and bacterial endotoxin are commercially available.

The invention is further described in the following example, which does not limit the scope of the invention described in the claims.

EXAMPLE

It has been reported that circulating concentrations of both the interleukin-1 receptor like 1 family member ST2 and galectin-3 are elevated in patients with heart failure (HF) and are independently prognostic. Experiments were performed to investigate the utility of ST2 measurement in patients with elevated concentrations of galectin-3.

The subjects used in this Example took part in the ProBNP Investigation of Dyspnea in the Emergency Department (PRIDE) Study, a prospective, blinded study of 599 dyspneic subjects presenting to the ED of the Massachusetts General Hospital, which was performed for the purpose of validating the diagnostic and prognostic use of NT-proBNP testing. The results of the PRIDE study were recently reported (Januzzi et al., Am. J. Cardiol. 95(8):948-954 (2005)).

The gold standard for the diagnosis of acute HF was based on the impression of reviewing physicians, blinded to NT-proBNP values, who had all available information from presentation through a 60-day follow-up period; for the few patients in whom a diagnosis was uncertain, the reviewers were instructed to utilize the guidelines as reported by the Framingham Heart Study (McKee et al., N. Engl. J. Med. 285(26):1441-1446 (1971)).

As reported, 209 subjects (35%) in the PRIDE study were adjudicated to have dyspnea due to acute destabilized HF, of whom 17 had mild (Class II) symptoms by the New York Heart Association (NYHA) classification, 80 had moderate (Class III) symptoms, and 112 had severe (Class IV symptoms).

At the end of one year, the managing physician for each patient was contacted for the purposes of ascertainment of vital status. As reported, follow-up at one year was complete in 597 subjects overall.

Blood collected at the time of presentation was later analyzed for concentrations of ST2, using an enzyme-linked immunosorbent assay (Critical Diagnostics, San Diego), as described herein. This assay utilizes monoclonal antibodies to human ST2 for both capture and detection, and had an inter-assay coefficient of variation of <10% in the present analysis. Galectin-3 was analyzed using a commercially available enzyme-linked immunosorbent assay kit (Bender Medsystems, Vienna, Austria) and was measured on a Victor 2 plate reader (Perkin Elmer, Turku, Finland). Calibration of the assay was performed according to the manufacturer's protocol. Values were normalized to a standard curve. The intra-assay and inter-assay variances for galectin-3 were 5.6% and 8.6%, respectively. The blood used for the present study had been previously subjected to a single freeze-thaw cycle.

Distribution of Analyte Values

In this cohort of 209 patients with heart failure galectin-3 values were produced from 200 patients and soluble ST2 values were produced from 204 patients. Both analytes showed a non-normal distribution so subsequent risk analysis models will be based on either median values, a value corresponding to the upper percentile of normal or as log (natural log) transformed, continuous variables (Table 2). As shown in Table 1, a concentration for soluble ST2 of 35 ng/mL is above the 90th percentile of normal.

TABLE 2

Analyte Median and IQR values

| | N | Median (ng/mL) | 25-75 P | Normal Distr. |
|---|---|---|---|---|
| Galectin-3 | 200 | 9.2 | 7.4-12.0 | <0.0001 |
| ST2 | 204 | 42.7 | 26.9-78.7 | <0.0001 |

Risk Analysis

In this study cohort both analytes, soluble ST2 and galectin-3, were significant predictors of risk of mortality within 1 year as evaluated in a Cox proportional hazards regression model with each analyte used as a log transformed, continuous variable (Tables 3A and 3B). In this analysis, soluble ST2 has a higher (stronger) hazard ratio (HR), but both are statistically significant.

TABLE 3A

Univariate Cox HR Model; Mortality Within 1 Year

| Covariate | P | HR | 95% CI of HR |
|---|---|---|---|
| Ln ST2 | <0.0001 | 2.12 | 1.58 to 2.85 |
| Ln Galectin-3 | 0.0249 | 1.78 | 1.08 to 2.94 |

TABLE 3B

Univariate Cox HR Model; Mortality Within 4 Years

| Covariate | P | HR | 95% CI of HR |
|---|---|---|---|
| Ln ST2 | 0.0001 | 1.53 | 1.23 to 1.91 |
| Ln Galectin-3 | 0.0089 | 1.63 | 1.13 to 2.36 |

In a multivariate Cox proportional hazards regression model with each analyte used as a log transformed, continuous variable both analytes are significant for risk of mortality within 4 years, however galectin-3 is no longer statistically significant for risk of mortality within 1 year, while soluble ST2 remains strongly predictive (Tables 4A and 4B).

TABLE 4A

Multivariate Cox HR Model; Mortality Within 1 Year

| Covariate | P | HR | 95% CI of HR |
|---|---|---|---|
| Ln ST2 | <0.0001 | 2.07 | 1.54 to 2.79 |
| Ln Galectin-3 | 0.0818 | 1.63 | 0.94 to 2.81 |

TABLE 4B

Multivariate Cox HR Model; Mortality Within 4 Years

| Covariate | P | HR | 95% CI of HR |
|---|---|---|---|
| Ln ST2 | 0.0006 | 1.49 | 1.19 to 1.86 |
| Ln Galectin-3 | 0.0321 | 1.52 | 1.04 to 2.23 |

Both analytes were also tested for significance to predict risk in a 30 day follow up period. As was observed for the longer 1-year follow up period, both analytes are significant predictors of all-cause mortality in a univariate Cox proportional hazards regression model with each analyte used as a log transformed, continuous variable (Table 5).

TABLE 5

Univariate Cox HR Model; Mortality Within 30 Days

| Covariate | P | HR | 95% CI of HR |
|---|---|---|---|
| Ln ST2 | 0.0001 | 3.50 | 1.84 to 6.65 |
| Ln Galectin-3 | 0.0030 | 3.41 | 1.52 to 7.61 |

In the shorter follow up model, galectin-3 retains significance when soluble ST2 is also included in the model (Table 6).

TABLE 6

Multivariate Cox HR Model; Mortality Within 30 Days

| Covariate | P | HR | 95% CI of HR |
|---|---|---|---|
| Ln ST2 | 0.0003 | 3.27 | 1.73 to 6.20 |
| Ln Galectin-3 | 0.0148 | 3.34 | 1.27 to 8.77 |

Each analyte was also evaluated for risk of all-cause mortality within 1 year and 4 years by Kaplan-Meier (K-M) analysis using the cohort median value for each. As shown in FIGS. 1A and 1B, when analyzed by the median concentration value galectin-3 is not a significant predictor of all-cause mortality risk within 1 year but does reach significance over 4 years. However, as shown in FIGS. 2A and 2B, soluble ST2 is a strongly significant predictor of all-cause mortality risk within both 1 year and 4 years. ST2 was also evaluated by K-M analysis using the lower concentration of 35 ng/mL (FIG. 2C). As shown in FIG. 2C, soluble ST2 is a strongly significant predictor of mortality within 4 years.

To determine whether soluble ST2 adds predictive value in galectin-3 heart failure patients a subset of patients with galectin-3 concentrations greater than or equal to the cohort median concentration of 9.2 ng/mL were tested with soluble ST2. Table 7 shows the results from univariate Cox proportional hazards regression models with soluble ST2 used as a log transformed, continuous variable for assessment of all-cause mortality risk within 1 year and within 30 days. Soluble ST2 is strongly predictive in both time frames in galectin-3 heart failure patients.

TABLE 7

ST2 additive in galectin-3 HF patients (N = 98 patients)

| Covariate | P | HR | 95% CI of HR |
|---|---|---|---|
| Ln ST2 (1 year) | 0.0010 | 1.96 | 1.32 to 2.93 |
| Ln ST2 (30 days) | 0.0029 | 3.25 | 1.50 to 7.04 |

The opposite is not completely true however (see Tables 8A and 8B). In the subset of soluble ST2 heart failure patients, patients with soluble ST2 concentrations greater than or equal to the cohort median concentration of 42.7 ng/mL, or at the lower soluble ST2 concentration of 35 ng/mL, galectin-3 is not a significant predictor of all-cause mortality within 1 year, but does reach statistical significance for risk within 30 days as evaluated by Cox proportional hazards regression models (Tables 8A and 8B).

TABLE 8A

Galectin-3 additive to ST2 HF patients (ST2 ≥ median), N = 98

| Covariate | P | HR | 95% CI of HR |
|---|---|---|---|
| Ln Galectin-3 (1 year) | 0.2251 | 1.59 | 0.75 to 3.36 |
| Ln Galectin-3 (30 days) | 0.0214 | 4.10 | 1.24 to 13.53 |

TABLE 8B

Galectin-3 additive to ST2 HF patients (ST2 ≥ 35 ng/mL), N = 122

| Covariate | P | HR | 95% CI of HR |
|---|---|---|---|
| Ln Galectin-3 (1 year) | 0.4332 | 1.26 | 0.71 to 2.26 |
| Ln Galectin-3 (30 days) | 0.0467 | 2.44 | 1.02 to 5.86 |

These results are also illustrated in FIG. 3, and summarized in Table 9, where a K-M curve analysis of this cohort when the two analytes are combined (log rank p=0.0011). In this analysis in patients with concentrations below the median for both analytes the lowest risk profile is observed (line 1). When soluble ST2 is below median and galectin-3 is ≥median risk increases modestly (line 2). When galectin-3 is below median and soluble ST2 is ≥median risk increases significantly (line 3). And in patients with concentrations≥median for both analytes risk is the greatest.

TABLE 9

Summary of K-M Analysis Shown in FIG. 3

| | Bin | | | |
|---|---|---|---|---|
| Factor | 1 | 2 | 3 | 4 |
| N | 62 | 43 | 45 | 57 |
| N decedant | 8 | 11 | 17 | 24 |
| % decedant | 12.9% | 25.6% | 37.8% | 42.1% |

A number of embodiments of the invention have been described. Nevertheless, it will be understood that various modifications may be made without departing from the spirit and scope of the invention. Accordingly, other embodiments are within the scope of the following claims.

What is claimed is:

1. A method for evaluating the risk of an adverse clinical outcome (ACO) in a subject having heart failure, the method comprising:
   (a) performing an assay to determine a level of galectin-3 in a biological sample from a subject having heart failure,
   (b) comparing the level of galectin-3 in the biological sample of (a) to a reference level of galectin-3;
   (c) selecting a subject having an elevated level of galectin-3 in the biological sample of (a) as compared to the reference level of galectin-3;
   (d) performing an assay to determine a level of soluble ST2 in a biological sample from the selected subject;
   (e) comparing the level of soluble ST2 in the biological sample of (d) to a reference level of soluble ST2; and
   (f) identifying a selected subject having an elevated level of soluble ST2 in the biological sample of (d) as compared to the reference level of soluble ST2 as having an increased risk of an ACO as compared to a subject having heart failure and an elevated level of galectin-3, who has a non-elevated level of soluble ST2, or identifying a selected subject having a non-elevated level of soluble ST2 in the biological sample of (d) as compared to the reference level of soluble ST2 as having a decreased risk of an ACO as compared to a subject having heart failure and an elevated level of galectin-3, who has an elevated level of soluble ST2.

2. The method of claim 1, wherein the ACO is a rehospitalization, recurrence of one or more physical symptoms associated with angina, cardiovascular disease, or heart failure, an increase in the severity of one or more physical symptoms associated with a disease state, an increase in the frequency of one or more physical symptoms associated with a disease state, mortality, admission to a health care facility, or organ transplant.

3. The method of claim 2, wherein the rehospitalization or admission is for cardiovascular disease.

4. The method of claim 2, wherein the mortality is mortality due to cardiovascular disease.

5. The method of claim 1, wherein the risk of an ACO is within 1 year.

6. The method of claim 5, wherein the risk of an ACO is within 30 days.

7. The method of claim 1, wherein the sample comprises serum, blood, or plasma.

8. The method of claim 7, wherein the sample is serum.

9. The method of claim 1, wherein the biological sample of (a) and the biological sample of (d) are obtained from the subject at the same time.

10. The method of claim 1, wherein the subject has a BMI of 25-29, a BMI of ≥30, or renal insufficiency.

11. The method of claim 1, wherein the reference level of soluble ST2 is a level of soluble ST2 in a subject that does not have high risk cardiovascular disease.

12. The method of claim 1, wherein the reference level of galectin-3 is a level of galectin-3 in a subject that does not have high risk cardiovascular disease.

13. The method of claim 1, wherein the reference level of soluble ST2 or the reference level of galectin-3 is a threshold level of soluble ST2 or galectin-3.

14. The method of claim 1, wherein the method further comprises determining the level of one or more additional markers in the subject.

15. The method of claim 14, wherein the one or more additional markers are selected from the group consisting of: proANP, NT-proANP, ANP, proBNP, NT-proBNP, BNP, troponin, CRP, creatinine, Blood Urea Nitrogen (BUN), liver function enzymes, albumin, and bacterial endotoxin.

16. The method of claim 1, wherein the subject is human.

17. The method of claim 1, wherein a selected subject is identified as having an increased risk of an ACO as compared to a subject having heart failure and an elevated level of galectin-3, who has a non-elevated level of soluble ST2.

18. The method of claim 1, wherein a selected subject is identified as having a decreased risk of an ACO as compared to a subject having heart failure and an elevated level of galectin-3, who has an elevated level of soluble ST2.

19. A method for deciding whether to discharge or continue treating a subject having heart failure on an inpatient basis, comprising the steps of:
   (a) performing an assay to determine a level of galectin-3 in a biological sample from a subject having heart failure;
   (b) comparing the level of galectin-3 in the biological sample of (a) to a reference level of galectin-3;
   (c) selecting a subject who has an elevated level of galectin-3 in the biological sample of (a) as compared to the reference level of galectin-3;
   (d) performing an assay to determine a level of soluble ST2 in a biological sample from the selected subject;
   (e) comparing the level of soluble ST2 in the biological sample of (d) to a reference level of soluble ST2; and
   (f) determining that a selected subject having an elevated level of soluble ST2 in the biological sample of (d) as compared to the reference level of soluble ST2 should receive continued treatment on an inpatient basis, or that a selected subject having a non-elevated level of soluble ST2 in the biological sample of (d) as compared to the reference level of soluble ST2 should be discharged from inpatient treatment.

20. A method of selecting a subject having heart failure for participation in a clinical study of a treatment for heart failure, comprising the steps of:
   (a) performing an assay to determine a level of galectin-3 in a biological sample from a subject having heart failure;
   (b) comparing the level of galectin-3 in the biological sample of (a) to a reference level of galectin-3;
   (c) identifying a subject having an elevated level of galectin-3 in the biological sample of (a) as compared to the reference level of galectin-3;

(d) performing an assay to determine a level of soluble ST2 in a biological sample from the identified subject;
(e) comparing the level of soluble ST2 in the biological sample of (d) to a reference level of soluble ST2; and
(f) selecting an identified subject having an elevated level of soluble ST2 in the biological sample of (d) as compared to the reference level of soluble ST2 for participation in a clinical study of a treatment for heart failure.

21. A method for selecting a therapeutic treatment for a subject having heart failure comprising the steps of:
(a) performing an assay to determine a level of galectin-3 in a biological sample from a subject having heart failure;
(b) comparing the level of galectin-3 in the biological sample of (a) to a reference level of galectin-3;
(c) identifying a subject having an elevated level of galectin-3 in the biological sample of (a) as compared to the reference level of galectin-3;
(d) performing an assay to determine the level of soluble ST2 in a biological sample from the identified subject;
(e) comparing the level of soluble ST2 in the biological sample of (d) to a reference level of soluble ST2; and
(f) selecting inpatient treatment for an identified subject having an elevated level of soluble ST2 in the biological sample of (d) as compared to the reference level of soluble ST2, or selecting outpatient treatment for an identified subject having a non-elevated level of soluble ST2 in the biological sample of (d) as compared to the reference level of soluble ST2.

22. The method of claim 21, wherein the outpatient treatment comprises administration of a therapeutic agent selected from the group consisting of: nitrates, calcium channel blockers, diuretics, thrombolytic agents, digitalis, renin-angiotensin-aldosterone system (RAAS) modulating agents, and cholesterol-lowering agents.

23. The method of claim 22, wherein the cholesterol-lowering agent is a statin.

24. The method of claim 21, wherein inpatient treatment is selected for an identified subject having an elevated level of soluble ST2 as compared to the reference level of soluble ST2.

25. The method of claim 21, wherein outpatient treatment is selected for an identified subject having a non-elevated level of soluble ST2 as compared to the reference level of soluble ST2.

26. The method of claim 25, wherein the outpatient treatment comprises administration of a therapeutic agent selected from the group consisting of: nitrates, calcium channel blockers, diuretics, thrombolytic agents, digitalis, renin-angiotensin-aldosterone system (RAAS) modulating agents, and cholesterol-lowering agents.

27. A method for evaluating the risk of an adverse clinical outcome (ACO) in a subject having heart failure, the method comprising:
(a) selecting a subject having heart failure and an elevated level of galectin-3 as compared to the reference level of galectin-3;
(d) performing an assay to determine a level of soluble ST2 in a biological sample from the selected subject;
(e) comparing the level of soluble ST2 in the biological sample to a reference level of soluble ST2; and
(f) identifying a selected subject having an elevated level of soluble ST2 in the biological sample as compared to the reference level of soluble ST2 as having an increased risk of an ACO as compared to a subject having heart failure and an elevated level of galectin-3, who has a non-elevated level of soluble ST2; or identifying a selected subject having a non-elevated level of soluble ST2 in the biological sample as compared to the reference level of soluble ST2 as having a reduced risk of an ACO as compared to a subject having heart failure and an elevated level of galectin-3, who has an elevated level of soluble ST2.

28. The method of claim 27, wherein a selected subject is identified as having an increased risk of an ACO as compared to a subject having heart failure and an elevated level of galectin-3, who has a non-elevated level of soluble ST2.

29. The method of claim 27, wherein a selected subject is identified as having a decreased risk of an ACO as compared to a subject having heart failure and an elevated level of galectin-3, who has an elevated level of soluble ST2.

30. A method for selecting a therapeutic treatment for a subject having heart failure comprising the steps of:
(a) identifying a subject having an heart failure and an elevated level of galectin-3 as compared to the reference level of galectin-3 ;
(b) performing an assay to determine the level of soluble ST2 in a biological sample from the identified subject;
(c) comparing the level of soluble ST2 in the biological sample to a reference level of soluble ST2; and
(d) selecting inpatient treatment for an identified subject having an elevated level of soluble ST2 in the biological sample as compared to the reference level of soluble ST2, or selecting outpatient treatment for an identified subject having a non-elevated level of soluble ST2 in the biological sample as compared to the reference level of soluble ST2.

31. The method of claim 30, wherein inpatient treatment is selected for an identified subject having an elevated level of soluble ST2 as compared to the reference level of soluble ST2.

32. The method of claim 30, wherein outpatient treatment is selected for an identified subject having a non-elevated level of soluble ST2 as compared to the reference level of soluble ST2.

33. The method of claim 32, wherein the outpatient treatment comprises administration of a therapeutic agent selected from the group consisting of: nitrates, calcium channel blockers, diuretics, thrombolytic agents, digitalis, renin-angiotensin-aldosterone system (RAAS) modulating agents, and cholesterol-lowering agents.

* * * * *

UNITED STATES PATENT AND TRADEMARK OFFICE
CERTIFICATE OF CORRECTION

PATENT NO.        : 8,728,742 B2                                        Page 1 of 1
APPLICATION NO.   : 13/422574
DATED             : May 20, 2014
INVENTOR(S)       : James V. Snider It is certified that error appears in the above-identified patent and that said Letters Patent is hereby corrected as shown below:

In the Claims

Col. 40, line 29, in claim 30, delete "galectin-3 ;" and insert -- galectin-3; --.

Signed and Sealed this
Twelfth Day of August, 2014

Michelle K. Lee
*Deputy Director of the United States Patent and Trademark Office*